(12) United States Patent
Kadow et al.

(10) Patent No.: US 9,834,566 B2
(45) Date of Patent: Dec. 5, 2017

(54) PYRAZOLOPYRIMIDINE MACROCYCLES AS INHIBITORS OF HUMAN IMMUNODEFICIENCY VIRUS REPLICATION

(71) Applicant: VIIV HEALTHCARE UK (NO.5) LIMITED, Brentford, Middlesex (GB)

(72) Inventors: John F. Kadow, Wallingford, CT (US); B. Narasimhulu Naidu, Wallingford, CT (US); Manoj Patel, Wallingford, CT (US); Kevin Peese, Wallingford, CT (US); Tao Wang, Wallingford, CT (US); Zhiwei Yin, Wallingford, CT (US); Zhongxing Zhang, Wallingford, CT (US)

(73) Assignee: ViiV HEALTHCARE UK (NO.5) LIMITED, Brentford, Middlesex (GB)

( * ) Notice: Subject to any disclaimer, the term of this patent is extended or adjusted under 35 U.S.C. 154(b) by 0 days.

(21) Appl. No.: 15/119,431

(22) PCT Filed: Feb. 13, 2015

(86) PCT No.: PCT/US2015/015758
§ 371 (c)(1),
(2) Date: Aug. 17, 2016

(87) PCT Pub. No.: WO2015/126743
PCT Pub. Date: Aug. 27, 2015

(65) Prior Publication Data
US 2017/0057977 A1    Mar. 2, 2017

Related U.S. Application Data

(60) Provisional application No. 61/940,952, filed on Feb. 18, 2014.

(51) Int. Cl.
| C07D 498/16 | (2006.01) |
| C07D 498/22 | (2006.01) |
| A61K 31/519 | (2006.01) |
| A61K 45/06 | (2006.01) |

(52) U.S. Cl.
CPC .......... *C07D 498/16* (2013.01); *A61K 31/519* (2013.01); *A61K 45/06* (2013.01); *C07D 498/22* (2013.01)

(58) Field of Classification Search
CPC combination set(s) only.
See application file for complete search history.

(56) References Cited

U.S. PATENT DOCUMENTS

2014/0051692 A1*  2/2014  Naidu ............ A61K 31/519
                                                    514/229.5

FOREIGN PATENT DOCUMENTS

| WO | WO 2012/033735 A1 |   | 3/2012 |           |
| WO | WO 2014/008636 A1 |   | 1/2014 |           |
| WO | WO 2014/028384 A1 |   | 2/2014 |           |
| WO | WO 2015126376 A1  | * | 8/2015 | ........... C07D 498/16 |

OTHER PUBLICATIONS

Chemical Abstract Service (CAS) STN Registry Database Nos. 1567208-51-8 and 1567208-44-9 [entered STN: Mar. 12, 2014].*
Chemical Abstract Service (CAS) STN Registry Database Nos. 1567208-37-0, 1567208-21-2, 1567208-05-2 and 1567207-90-2 [entered STN: Mar. 12, 2014].*
Ferrara, et al. Tetrahedron Letters, 48(47): 8379-8382 (Oct. 24, 2007).

* cited by examiner

*Primary Examiner* — Michael Barker
*Assistant Examiner* — Amanda L Aguirre
(74) *Attorney, Agent, or Firm* — Robert H. Brink; Edward R. Gimmi; William R. Majarian

(57) ABSTRACT

The disclosure generally relates to compounds of formula I, including compositions and methods for treating human immunodeficiency virus (HIV) infection. The disclosure provides novel inhibitors of HIV integrase, pharmaceutical compositions containing such compounds, and methods for using these compounds in the treatment of HIV infection.

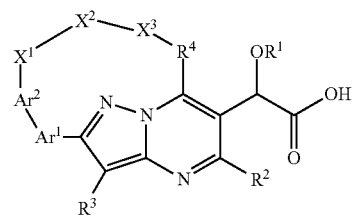

4 Claims, No Drawings

PYRAZOLOPYRIMIDINE MACROCYCLES AS INHIBITORS OF HUMAN IMMUNODEFICIENCY VIRUS REPLICATION

This application is a 371 of International Application No. PCT/US2015/015758, filed 13 Feb. 2015, which claims the benefit of U.S. Provisional Application No. 61/940,952, filed 18 Feb. 2014, which are incorporated herein in their entireties.

CROSS-REFERENCE TO RELATED APPLICATIONS

This application claims priority to Provisional Patent Application U.S. Ser. No. 61/940,952 filed Feb. 18, 2014, hereby incorporated by reference in its entirety.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that as many as 35.3 million people worldwide are infected with the virus (UNAIDS Report on the Global AIDS Epidemic 2013). In addition to the large number of individuals already infected, the virus continues to spread. Estimates from 2012 point to close to 2.3 million new infections in that year alone. In the same year there were approximately 1.6 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: However, the effect is only temporary as the virus readily develops resistance to all known agents used as monotherapy. On the other hand, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2007131350, WO2009062285, WO2009062288, WO2009062289, WO2009062308, WO2010130842, WO2011076765, WO2012003497, WO2012003498, WO2012033735, WO2012065963, WO2012066442, WO2013012649, WO2013043553, WO2013062028, WO2013073875, WO2013134113, WO2013134142, WO2014021867, WO20140028384, WO2014164428.

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I

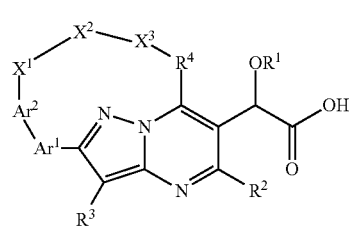

I where:
$R^1$ is hydrogen, alkyl, or cycloalkyl;
$R^2$ is hydrogen or alkyl;
$R^3$ is hydrogen, alkyl or halo;
$R^4$ is cycloalkyl or $Ar^3$;
or $R^4$ is azetidinyl, pyrrolidinyl, piperidinyl, piperazinyl, morpholinyl, homopiperidinyl, homopiperazinyl, or homomorpholinyl, and is substituted with 0-3 alkyl substituents;
$R^5$ is independently hydrogen, alkyl, or $(Ar^4)$alkyl;
$R^6$ is O, $NR^7$, phenyl, or pyridinyl;
$R^7$ is hydrogen, alkyl, or benzyl;

Ar$^1$ is phenyl substituted with 0-3 substituents selected from cyano, halo, alkyl, haloalkyl, alkoxy, and haloalkoxy;
Ar$^2$ is phenyl, pyridinyl, pyridazinyl, pyrimidinyl, pyrazinyl, or triazinyl, and is substituted with 0-3 substituents selected from cyano, halo, alkyl, haloalkyl, alkoxy, haloalkoxy, and CON(R$^5$)$_2$;
Ar$^3$ is phenyl, napthyl, chromanyl, or dihydrobenzoxazinyl, and is substituted with 0-3 substituents selected from cyano, halo, alkyl, haloalkyl, alkoxy, and haloalkoxy;
Ar$^4$ is phenyl substituted with 0-3 substituents selected from cyano, halo, alkyl, haloalkyl, alkoxy, and haloalkoxy;
X$^1$ is CH, CH$_2$, O, S, or NR$^5$;
X$^2$ is alkylene, alkenylene, alkynylene, haloalkylene, or —(CH$_2$)$_{0-3}$—R$^6$—(CH$_2$)$_{0-3}$—; and
X$^3$ is CH, CH$_2$, CH$_2$O, O, S, or NR$^5$;
or a pharmaceutically acceptable salt thereof.

Another aspect of the invention is a compound of formula I where
R$^1$ is hydrogen, alkyl, or cycloalkyl;
R$^2$ is hydrogen or alkyl;
R$^3$ is hydrogen, alkyl or halo;
R$^4$ is cycloalkyl or Ar$^3$;
or R$^4$ is azetidinyl, pyrrolidinyl, piperidinyl, piperazinyl, morpholinyl, homopiperidinyl, homopiperazinyl, or homomorpholinyl, and is substituted with 0-3 alkyl substituents;
R$^5$ is hydrogen or alkyl;
R$^6$ is O, NR$^7$, phenyl, or pyridinyl;
R$^7$ is hydrogen, alkyl, or benzyl;
Ar$^1$ is phenyl substituted with 0-3 substituents selected from cyano, halo, alkyl, haloalkyl, alkoxy, and haloalkoxy;
Ar$^2$ is phenyl, pyridinyl, pyridazinyl, pyrimidinyl, pyrazinyl, or triazinyl, and is substituted with 0-3 substituents selected from cyano, halo, alkyl, haloalkyl, alkoxy, haloalkoxy, and CON(R$^5$)$_2$;
Ar$^3$ is phenyl, napthyl, chromanyl, or dihydrobenzoxazinyl, and is substituted with 0-3 substituents selected from cyano, halo, alkyl, haloalkyl, alkoxy, and haloalkoxy;
X$^1$ is CH, CH$_2$, O, S, or NR$^5$;
X$^2$ is alkynylene, haloalkylene, or —(CH$_2$)$_{0-3}$—R$^6$—(CH$_2$)$_{0-3}$—; and
X$^3$ is CH, CH$_2$, CH$_2$O, O, S, or NR$^5$;
or a pharmaceutically acceptable salt thereof.

Another aspect of the invention is a compound of formula I where R$^1$ is alkyl; R$^2$ is alkyl; R$^3$ is hydrogen; R$^4$ is Ar$^3$ or is azetidinyl, pyrrolidinyl, piperidinyl, piperazinyl, morpholinyl, homopiperidinyl, homopiperazinyl, or homomorpholinyl substituted with 0-3 alkyl substituents; R$^5$ is hydrogen or alkyl; R$^6$ is O, NR$^7$, phenyl, or pyridinyl; R$^7$ is hydrogen, alkyl, or benzyl; Ar$^1$ is phenyl substituted with 0-3 substituents selected from cyano, halo, alkyl, haloalkyl, alkoxy, and haloalkoxy; Ar$^2$ is phenyl substituted with 0-3 substituents selected from selected from cyano, halo, alkyl, haloalkyl, alkoxy, haloalkoxy, and CON(R$^5$)$_2$; Ar$^3$ is phenyl, napthyl, or chromanyl, and is substituted with 0-3 substituents selected from cyano, halo, alkyl, haloalkyl, alkoxy, and haloalkoxy; X$^1$ is CH$_2$ or O; X$^2$ is alkynylene, haloalkylene, or —(CH$_2$)$_{0-3}$—R$^6$—(CH$_2$)$_{0-3}$—; and X$^3$ is CH, CH$_2$ or O; or a pharmaceutically acceptable salt thereof.

Another aspect of the invention is a compound of formula I where R$^4$ is Ar$^3$ or piperidinyl substituted with 0-3 alkyl substituents; R$^6$ is O, NR$^7$, phenyl, or pyridinyl; R$^7$ is hydrogen, alkyl, or benzyl; Ar$^1$ is phenyl substituted with 0-3 substituents selected from cyano, halo, alkyl, haloalkyl, alkoxy, and haloalkoxy; Ar$^2$ is phenyl substituted with 0-3 substituents selected from selected from cyano, halo, alkyl, haloalkyl, alkoxy, and haloalkoxy; Ar$^3$ is phenyl, napthyl, or chromanyl, and is substituted with 0-3 substituents selected from cyano, halo, alkyl, haloalkyl, alkoxy, and haloalkoxy; X$^1$ is CH$_2$ or O; X$^2$ is haloalkylene or —(CH$_2$)$_{0-3}$—R$^6$—(CH$_2$)$_{0-3}$—; and X$^3$ is CH, CH$_2$ or O; or a pharmaceutically acceptable salt thereof.

Another aspect of the invention is a compound of formula I where R$^1$ is alkyl, R$^2$ is alkyl and R$^3$ is hydrogen.

Another aspect of the invention is a compound of formula I where R$^4$ is Ar$^3$.

Another aspect of the invention is a compound of formula I where R$^4$ is piperidinyl substituted with 0-3 alkyl substituents.

Another aspect of the invention is a compound of formula I where Ar$^1$ is phenyl.

Another aspect of the invention is a compound of formula I where Ar$^2$ is phenyl substituted with 0-3 substituents selected from cyano, halo, alkyl, haloalkyl, alkoxy, and haloalkoxy.

Another aspect of the invention is a compound of formula I where Ar$^3$ is phenyl, naphthyl, or chromanyl, and is substituted with 0-3 substituents selected from cyano, halo, alkyl, haloalkyl, alkoxy, and haloalkoxy.

Another aspect of the invention is a compound of formula I where X$^1$ is O; X$^2$ is —(CH$_2$)$_{0-3}$—R$^6$—(CH$_2$)$_{0-3}$—; and X$^3$ is O.
or a pharmaceutically acceptable salt thereof.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkylene" means a straight or branched divalent alkyl group composed of 1 to 6 carbons. "Alkenylene" means a straight or branched divalent alkene group composed of 2 to 6 carbons with at least one double bond. "Alkynylene" means a straight or branched divalent alkyne group composed of 2 to 6 carbons with at least one triple bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Alkyleneoxy" means a straight or branched divalent alkyloxy group composed of 1 to 6 carbons, for example, —CH$_2$CH$_2$CH$_2$O—. "Alkenyleneoxy" means a straight or branched divalent alkeneoxy group composed of 2 to 6 carbons with at least one double bond, for example, —CH=CHCH$_2$O—. "Alkynyleneoxy" means a straight or branched divalent alkyneoxy group composed of 2 to 6 carbons with at least one double bond, for example, —CC—CH$_2$O—. "Halo" includes fluoro, chloro, bromo, and iodo. "Halo" includes all halogenated isomers from monohalo substituted to perhalo substituted in substituents defined with halo, for example, "Haloalkyl" "haloalkoxy", "halophenyl", and "halophenoxy." "Aryl" includes carbocyclic and heterocyclic aromatic substituents. Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV Replication:

A recombinant NL-RLuc proviral clone was constructed in which a section of the nef gene from NL4-3 was replaced with the *Renilla* Luciferase gene. This virus is fully infectious and can undergo multiple cycles of replication in cell culture. In addition, the luciferous reporter provides a simple and easy method for quantitating the extent of virus growth and consequently, the antiviral activity of test compounds. The plasmid pNLRLuc contains the proviral NL-Rluc DNA cloned into pUC18 at the PvuII site. The NL-RLuc virus was prepared by transfection of 293T cells with the plasmid pNLRLuc. Transfections were performed using the LipofectAMINE PLUS kit from Invitrogen (Carlsbad, Calif.) according to the manufacturer and the virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. Assay media was RPMI 1640 supplemented with 10% heat inactivated fetal bovine serum (FBS), 100 units/ml penicillin G/100 units/ml streptomycin, 10 mM HEPES buffer pH 7.55 and 2 mM L-glutamine. The results from at least 2 experiments were used to calculate the $EC_{50}$ values. Luciferase was quantitated using the Dual Luciferase kit from Promega (Madison, Wis.). Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press. 1990). Results are shown in Table 1.

TABLE 1

| Example | $EC_{50}$ μM |
|---|---|
| 1 | 0.397 |
| 2 | 0.696 |
| 3 | 0.055 |
| 4 | 0.281 |
| 5 | 0.309 |
| 6 | 20.000 |
| 7 | 12.110 |
| 8 | 0.784 |
| 9 | 0.489 |
| 10 | 4.199 |
| 11 | 3.312 |
| 12 | 1.666 |
| 13 | 0.288 |
| 14 | 3.250 |
| 15 | 0.301 |
| 16 | 0.780 |
| 17 | 0.289 |
| 18 | 1.140 |
| 19 | 3.589 |
| 20 | 2.781 |
| 21 | 0.695 |
| 22 | 1.445 |
| 23 | 0.123 |
| 24 | 0.006 |
| 25 | 0.004 |
| 26 | 0.003 |

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCM" for dichloromethane, "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "DEAD" for diethyl azodicarboxylate and "DIAD" for diisopropyl azodicarboxylate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds can be synthesized from an appropriately substituted heterocycle I-1 according to Scheme I, Compound I-1 and I-2 are commercially available or synthesized by reactions known in the art. Intermediates I-3 were prepared by procedure known in the art or as set forth in the examples below using compound I-1 and compound I-2. Intermediates I-3 were transformed to intermediates I-5 via intermediates I-4 using conditions known to those skilled in the art. Intermediates I-5 were oxidized to intermediates I-6 by reactions known in the art, including Des-Martin oxidation. Intermediates I-6 were reduced to chiral intermediates I-7 using known conditions in the presence of catalytic chiral Lewis acid. Intermediates I-7 were converted to the intermediates I-8 by known conditions, including tertiary-butyl acetate and perchloric acid. Sequential coupling of aryl groups to Intermediates I-8 using conditions known in the art, including Suzuki coupling, provide intermediates I-9 and I-10. Boronate or boronic acid coupling reagents are commercially available or prepared by reactions known in the art.

Intermediates I-10 were converted to intermediates I-11 by conditions known in the art. Hydrolysis of intermediates I-11 by using conditions known in the art provided final products I-12.

Scheme I

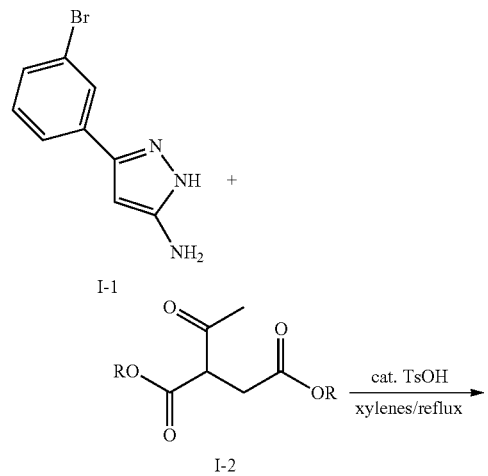

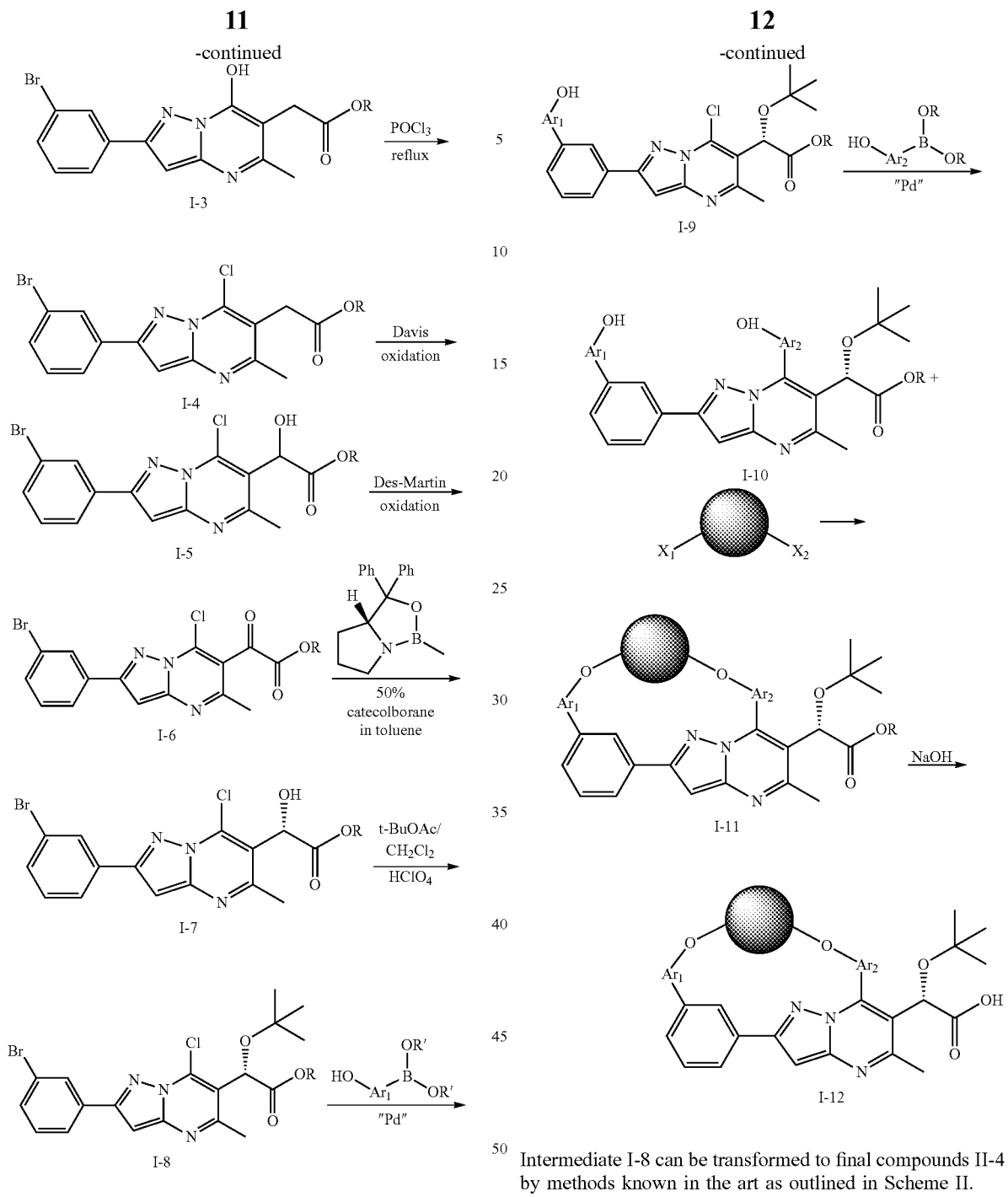
Intermediate I-8 can be transformed to final compounds II-4 by methods known in the art as outlined in Scheme II.
Scheme II
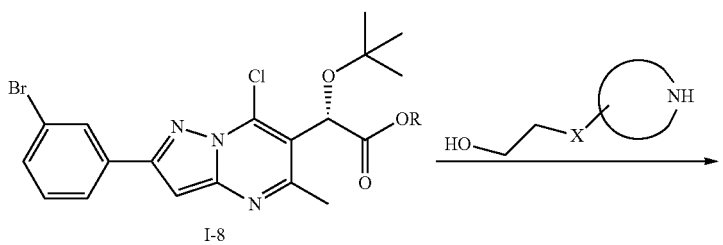

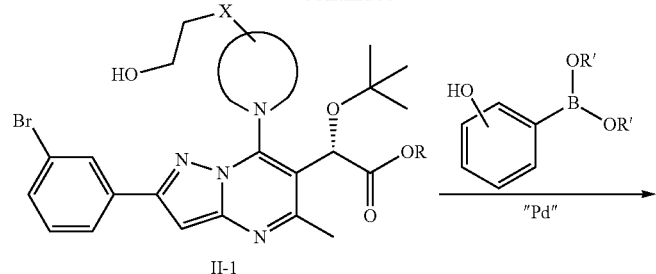
II-1
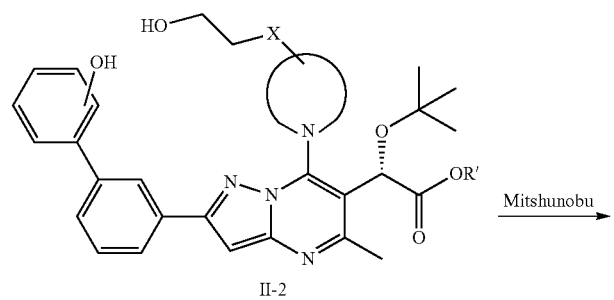
II-2
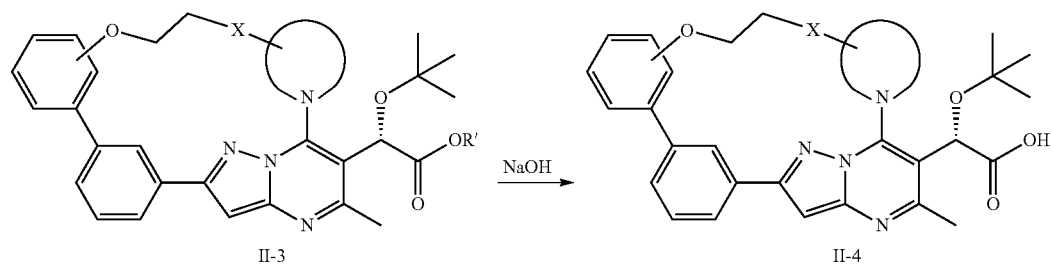
II-3                                II-4
Intermediates I-8 can be transformed to final compounds III-7 and III-8 by methods known in the art as outlined in Scheme III.
Scheme III
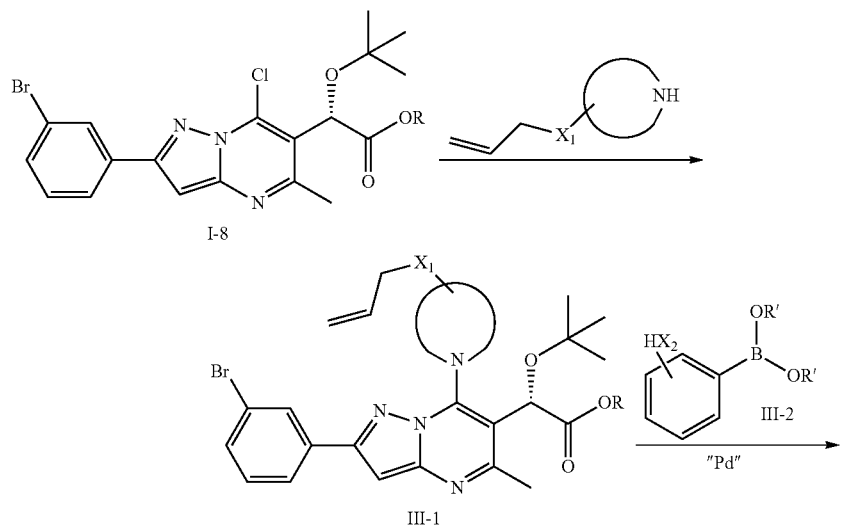
I-8
III-1

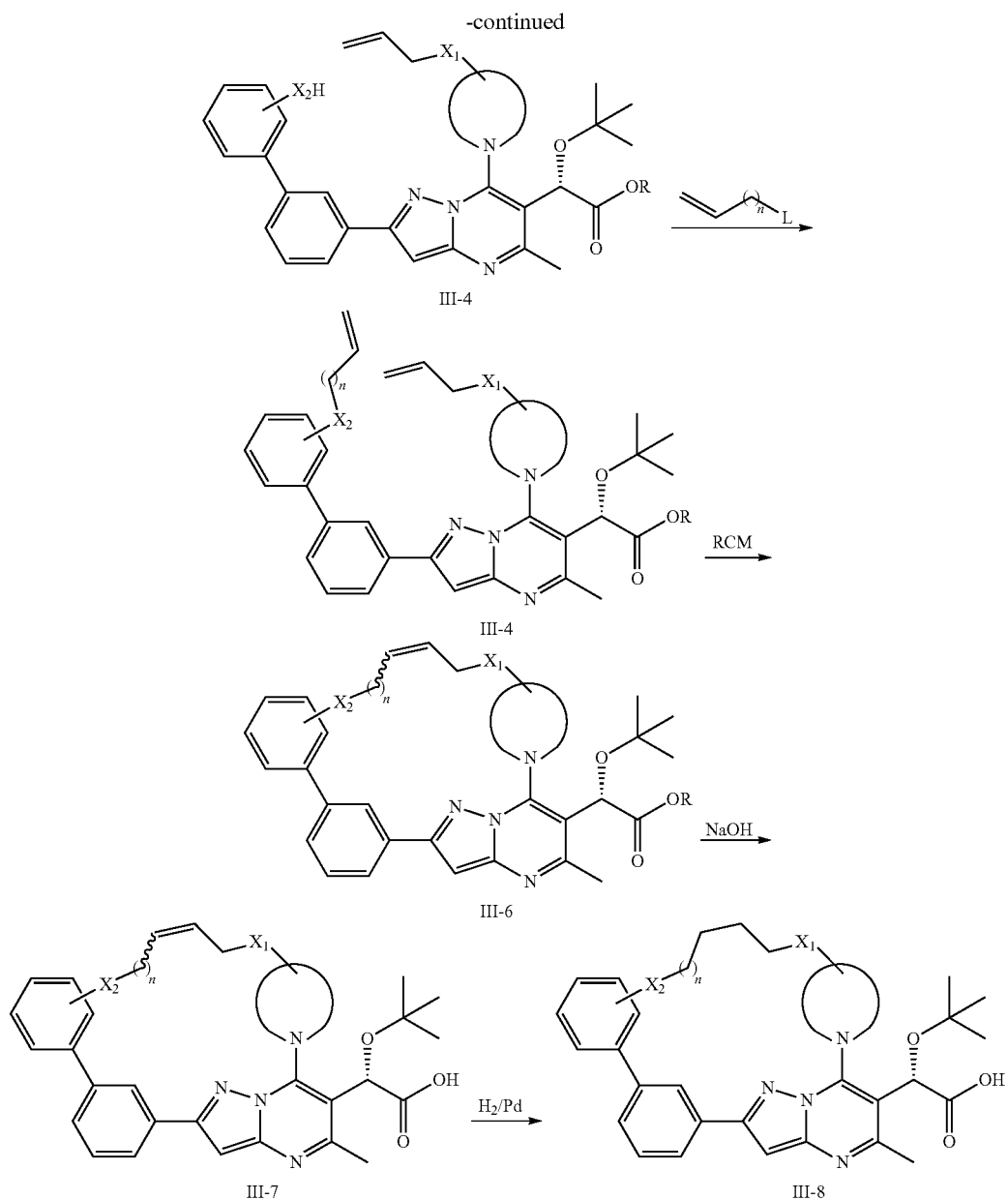

The compounds described herein were purified by the methods known to those skilled in art by normal phase column chromatography on silica gel column using appropriate solvent systems. Preparative HPLC purifications mentioned in this experimentation section were carried out by gradient elution on C, 18 prep-columns (5 μm) using either mobile phase A: 9:1 H₂O/acetonitrile with 10 mM NH₄OAc and mobile phase B: A: 9:1 acetonitrile/H₂O with: 10 mM NH₄OAc or mobile phase A: 95:5 H₂O/MeOH with 20 mM NH₄OAc and mobile phase B: 95:5 MeOH/H₂O with 20 mM NH₄OAc.

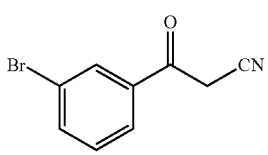 [SMILES: N#CCC(=O)c1cccc(Br)c1]

3-(3-bromophenyl)-3-oxopropanenitrile

Acetonitrile (21.86 mL, 419 mmol) was added to a stirred suspension of 60% NaH (7.25 g, 181 mmol) in THF (150 mL). Then, methyl 3-bromobenzoate (30 g, 140 mmol) was added and the mixture was heated at 75° C. for 4 h. After cooling to room temperature, water followed by 1N HCl (200 mL) was added and the mixture was extracted with ethyl acetate (500 mL), washed with sat. NaHCO₃ solution (200 mL), dried (Na₂SO₄), filtered and concentrated to afford 3-(3-bromophenyl)-3-oxopropanenitrile (29 g, 129 mmol, 93% yield) as light yellow solid. ¹H NMR (500 MHz, CDCl₃) δ 8.09 (t, J=1.7 Hz, 1H), 7.90-7.86 (m, 1H), 7.83 (ddd, J=8.0, 2.0, 1.1 Hz, 1H), 7.45 (t, J=7.9 Hz, 1H), 4.08 (s, 2H).

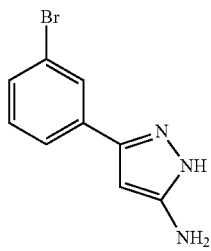 [SMILES: Nc1cc(-c2cccc(Br)c2)n[nH]1]

3-(3-bromophenyl)-1H-pyrazol-5-amine

A mixture of 3-(3-bromophenyl)-3-oxopropanenitrile (35 g, 156 mmol) and hydrazine hydrate (11.34 mL, 234 mmol) in ethanol (600 mL) was refluxed for 16 h. Mixture was then cooled and concentrated in vacuo. Crude product was diluted with dichloromethane and stirred for 5 min. Solids were filtered and dried to afford 3-(3-bromophenyl)-1H-pyrazol-5-amine (30 g, 126 mmol, 81% yield) as off-white solid. $^1$H NMR (400 MHz, DMSO-$d_6$) δ 12.02 (br. s., 0.4H), 11.66 (br. s., 0.6H), 7.86 (t, J=1.6 Hz, 1H), 7.67 (d, J=7.5 Hz, 1H), 7.45 (d, J=6.8 Hz, 1H), 7.37-7.18 (m, 1H), 5.78 (br. s., 1H), 5.08 (br. s., 1.2H), 4.68 (br. s., 0.8H). LCMS (M+H)=240.1.

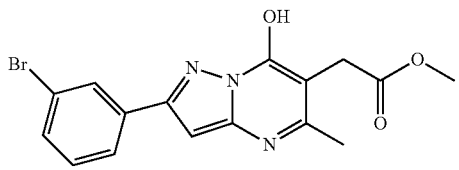 [SMILES: COC(=O)Cc1c(C)nc2cc(-c3cccc(Br)c3)nn2c1Cl]

Methyl 2-(2-(3-bromophenyl)-7-hydroxy-5-methyl-pyrazolo[1,5-a]pyrimidin-6-yl)acetate A 3-lit three neck flask was fitted with a mechanical stirrer and a heating mantle. A suspension of 3-(3-bromophenyl)-1H-pyrazol-5-amine (84.9 g, 357 mmol), dimethyl 2-acetylsuccinate (73.8 g, 392 mmol) and tosic acid monohydrate (1.357 g, 7.13 mmol) in o-xylene (1500 mL) was heated to refluxed (135° C. measured internal temp) for 3.5 h. The heating was turned off, the reaction was diluted with hexanes (1000 mL) and was allowed to cool slowly overnight. The solids were collected by filtration. The filter cake was washed with hexanes and dried under vacuum overnight to afford methyl 2-(2-(3-bromophenyl)-7-hydroxy-5-methyl-pyrazolo[1,5-a]pyrimidin-6-yl)acetate (132.21 g, 334 mmol, 94% yield) as a white powdery solid. $^1$H NMR (500 MHz, DMSO-$d_6$) δ: 12.47 (s, 1H), 8.18 (t, J=1.7 Hz, 1H), 8.02 (dt, J=7.1, 1.3 Hz, 1H), 7.65-7.60 (m, 1H), 7.45 (t, J=7.9 Hz, 1H), 6.69 (s, 1H), 3.63 (s, 3H), 3.58 (s, 2H), 2.34 (s, 3H). LCMS (M+H)=376.4.

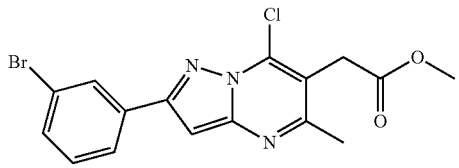

2-(2-(3-Bromophenyl)-7-chloro-5-methylpyrazolo[1,5-a]pyrimidin-6-yl)acetate

A mixture of methyl 2-(2-(3-bromophenyl)-7-hydroxy-5-methylpyrazolo[1,5-a]pyrimidin-6-yl)acetate (133 g, 354 mmol) and N,N-dimethylaniline (62.7 ml, 495 mmol) in POCl$_3$ (450 ml) was heated (120° C. oil bath) for 2.5 h. The reaction was cooled, then concentrated under reduced pressure. The residue was dried from toluene (3×300 mL), and the residue, suspended in EtOAc (600 mL) was poured onto ice water at a rate that maintained the cold temperature. The emulsion was then diluted (EtOAc, 300 mL) and the combined layers were pulled through a filter paper to collect solids. The solids were washed with several portions of EtOAc, then air dried. The filtered solids were suspended in EtOAc and hexanes (500 mL of each) and stirred for 10 min, then filtered. The filter cake was washed with hexanes and dried under vacuum to afford methyl 2-(2-(3-bromophenyl)-7-chloro-5-methylpyrazolo[1,5-a]pyrimidin-6-yl)acetate (121.7 g, 300 mmol, 85% yield) as pale green solid. $^1$H NMR (500 MHz, DMSO-$d_6$) δ: 8.25 (t, J=1.8 Hz, 1H), 8.09 (dt, J=7.8, 1.3 Hz, 1H), 7.63-7.70 (m, 1H), 7.45-7.54 (m, 1H), 7.40 (s, 1H), 4.04 (s, 2H), 3.71 (s, 3H), 2.58 (s, 3H). LC/MS (085-04, M+H)=396.1.

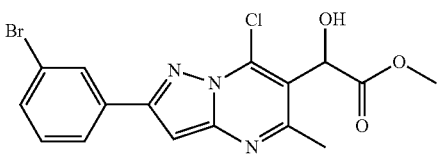

Methyl 2-(2-(3-bromophenyl)-7-chloro-5-methyl-pyrazolo[1,5-a]pyrimidin-6-yl)-2-hydroxyacetate To a stirred solution of 0.91M KHMDS/THF (95 mL, 95 mmol) in THF (50 mL) at −78° C. was added dropwise a solution of methyl 2-(2-(3-bromophenyl)-7-chloro-5-methylpyrazolo[1,5-a]pyrimidin-6-yl)acetate (25 g, 63.3 mmol) in THF (300 mL). After 1 h, 3-phenyl-2-(phenylsulfonyl)-1,2-oxaziridine (24.8 g, 95 mmol) in THF (100 mL) was added over the course of 10 min. This red reaction mixture was stirred at −78° C. for 2 h. Then, the resulting orange solution was quenched with sat. aq. NH$_4$Cl (400 mL), diluted with EtOAc (400 mL), and partitioned with a sep. funnel. The organic phase was washed with water and brine. The organic phase was dried (Na$_2$SO$_4$), filtered, and concentrated to give a light brown solid. Trituration with hexanes followed by trituration with ether (5×50 mL) gave 21 g of a yellow solid: methyl 2-(2-(3-bromophenyl)-7-chloro-5-methylpyrazolo[1,5-a]pyrimidin-6-yl)-2-hydroxyacetate (as a 1:1 complex with benzenesulfonamide). $^1$H NMR (400 MHz, CDCl3) δ 8.20 (t, J=1.8 Hz, 1H), 7.95 (dq, J=7.8, 0.8 Hz, 1H), 7.57 (ddd, J=8.0, 2.0, 1.0 Hz, 1H), 7.37 (t, J=7.9 Hz, 1H), 6.95 (s, 1H), 5.79 (s, 1H), 3.87 (s, 3H), 3.59 (d, J=1.8 Hz, 1H), 2.65 (s, 3H). LCMS (M+H)=410 and 412.

Methyl 2-(2-(3-bromophenyl)-7-chloro-5-methyl-pyrazolo[1,5-a]pyrimidin-6-yl)-2-oxoacetate To a stirred inseparable mixture of methyl 2-(2-(3-bromophenyl)-7-chloro-5-methylpyrazolo[1,5-a]pyrimidin-6-yl)-2-hydroxyacetate (12.9 g, 31.4 mmol) and benzenesulfonamide (2.96 g, 18.85 mmol) in CH$_2$Cl$_2$ (700 mL) was added Dess-Martin Periodinane (13.3 g, 31.4 mmol). Stir for 60 min at rt at which time the reaction appeared complete by TLC (1:1 hexane/EtOAc). The reaction was placed in the refrigerator for 2 h and then filtered through a medium fritted glass funnel. The brown homogeneous solution was treated with 140 mL of sat.aq. Na$_2$CO$_3$ and stirred rapidly for 30 min. The organic phase was separated and washed with additional sat.aq. Na$_2$CO$_3$ in a separatory funnel. The organic phase was dried (Na$_2$SO$_4$) and filtered through celite. The filtrate was then filtered through 170 g of silica gel with the aid of another 1 L of CH$_2$Cl$_2$. The light yellow filtrate was concentrated in vacuo to give 9.5 g of a yellow solid which after further drying gave 8.43 g (66%) of methyl 2-(2-(3-bromophenyl)-7-chloro-5-methylpyrazolo[1,5-a]pyrimidin-6-yl)-2-oxoacetate as a light yellow solid. $^1$H NMR (400 MHz, CDCl3) δ 8.21 (t, J=1.6 Hz, 1H), 7.96 (d, J=7.8 Hz, 1H), 7.60 (dt, J=8.0, 0.9 Hz, 1H), 7.39 (t, J=7.9 Hz, 1H), 7.02 (s, 1H), 4.03 (s, 3H), 2.65 (s, 3H). LCMS (M+H)=408 and 410.

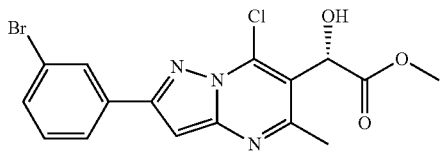 [SMILES: COC(=O)C(O)c1c(C)nc2cc(-c3cccc(Br)c3)nn2c1Cl]

(S)-Methyl 2-(2-(3-bromophenyl)-7-chloro-5-methylpyrazolo[1,5-a]pyrimidin-6-yl)-2-hydroxyacetate To a stirred solution of methyl 2-(2-(3-bromophenyl)-7-chloro-5-methylpyrazolo[1,5-a]pyrimidin-6-yl)-2-oxoacetate (14 g, 34.3 mmol) in anhydrous toluene (400 mL) was added 1.1M (R)-1-methyl-3,3-diphenylhexahydropyrrolo[1,2-c][1,3,2]oxazaborole/toluene (12.5 mL, 13.7 mmol). The mixture was cooled to −35° C. and then a 4.17M solution of catechoborane/toluene (11.7 mL, 48 mmol) was added over the course of 10 min. After 30 min, the reaction mixture was slowly warmed to −15° C. and stirred for additional 2 h. At this point the reaction mixture was diluted with EtOAc (300 mL) and treated with sat.aq. Na$_2$CO$_3$ (50 mL). The mixture was stirred vigorously for 10 min. The organic phase was separated and washed with sat. aq. Na$_2$CO$_3$ (5×100 mL), 0.1N HCl (1×100 mL), and brine. The organic phase was dried (Na$_2$SO$_4$), filtered, and concentrated. The residue was triturated with ether to obtain 12 g (77%) of the desired (S)-methyl 2-(2-(3-bromophenyl)-7-chloro-5-methylpyrazolo[1,5-a]pyrimidin-6-yl)-2-hydroxyacetate as a colorless oil. $^1$H NMR (400 MHz, CDCl$_3$) δ 8.20 (t, J=1.8 Hz, 1H), 7.95 (dq, J=7.8, 0.8 Hz, 1H), 7.57 (ddd, J=8.0, 2.0, 1.0 Hz, 1H), 7.37 (t, J=7.9 Hz, 1H), 6.95 (s, 1H), 5.79 (s, 1H), 3.87 (s, 3H), 3.59 (d, J=1.8 Hz, 1H), 2.65 (s, 3H). LCMS (M+H)=410 and 412.

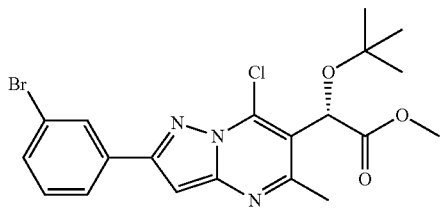 [SMILES: COC(=O)[C@@H](OC(C)(C)C)c1c(C)nc2cc(-c3cccc(Br)c3)nn2c1Cl]

(S)-Methyl 2-(2-(3-bromophenyl)-7-chloro-5-methylpyrazolo[1,5-a]pyrimidin-6-yl)-2-(tert-butoxy)acetate A mixture of (S)-methyl 2-(2-(3-bromophenyl)-7-chloro-5-methylpyrazolo[1,5-a]pyrimidin-6-yl)-2-hydroxyacetate (7.81 g, 19.02 mmol), t-butylacetate (160 mL) in DCM (330 mL) was added perchloric acid (3.43 mL, 57.1 mmol) and the mixture was stirred at rt for 3 h. It was then quenched with sat.aq. NaHCO$_3$ (adjusted to pH=7-8 by the addition of solid NaHCO$_3$). This mixture was diluted with EtOAc and the organic phase was washed with water. The organic phase was dried (MgSO$_4$), filtered, and concentrated in vacuo to obtain ~7 g of crude product as an oil. Filtration through 70 g of silica gel eluting with CH$_2$Cl$_2$ gave (S)-methyl 2-(2-(3-bromophenyl)-7-chloro-5-methylpyrazolo[1,5-a]pyrimidin-6-yl)-2-(tert-butoxy)acetate (5.71 g, 12.23 mmol, 64.3% yield). $^1$H NMR (400 MHz, CDCl$_3$) δ 8.20 (t, J=1.6 Hz, 1H), 7.95 (dt, J=7.8, 1.1 Hz, 1H), 7.63-7.53 (m, 1H), 7.37 (t, J=7.9 Hz, 1H), 6.94 (s, 1H), 5.69 (s, 1H), 3.76 (s, 3H), 2.70 (s, 3H), 1.30 (s, 9H). LCMS (M+H)=466 and 468.

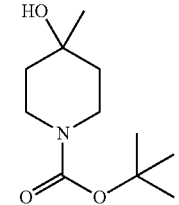

tert-Butyl 4-hydroxy-4-methylpiperidine-1-carboxylate

Under an N$_2$ atmosphere, a 3N MeMgBr/ether (1.67 mL, 5.02 mmol) was added dropwise to a cooled (−25° C.) solution of tert-butyl 4-hydroxy-4-methylpiperidine-1-carboxylate (4 g, 20.08 mmol) in ether (20 mL). The reaction mixture was allowed to warm to rt and was stirred for 2 h. It was then cooled to 0° C. and quenched by the addition of sat. NH$_4$Cl. Another 20 mL of ether was added and the mixture was partitioned in a separatory funnel. The organic phase was set aside and the aqueous phase was extracted with another 20 mL of ether. The combined ether extracts were dried over MgSO$_4$, filtered and evaporated to obtain an oil, which was then purified by BIOTAGE™ flash chromatography purification system, eluting with 0-50% EtOAc/hexane to obtain tert-butyl 4-hydroxy-4-methylpiperidine-1-carboxylate (4.30 g, 18.0 mmol, 90% yield) as a colorless oil. $^1$H NMR (500 MHz, CDCl$_3$) δ 3.84-3.65 (m, 2H), 3.34-3.18 (m, 2H), 2.59-2.39 (m, 1H), 1.61-1.53 (m, 4H), 1.50-1.45 (m, 9H), 1.32-1.27 (m, 3H).

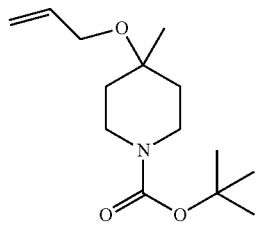 [SMILES: C=CCOC1(C)CCN(C(=O)OC(C)(C)C)CC1]

tert-Butyl 4-(allyloxy)-4-methylpiperidine-1-carboxylate

To a mixture of tert-butyl 4-hydroxy-4-methylpiperidine-1-carboxylate (4.30 g, 20.0 mmol) in DMF (50 mL) at 0° C. was added NaH (60 wt %) (1.60 g, 39.9 mmol). The mixture was then stirred at rt for 2 h. At this time allyl bromide (8.64 mL, 100 mmol) was added slowly over the course of 5 min. The reaction mixture was stirred at rt for 3 h. It was then cooled to 0° C. and quenched with sat. NH$_4$Cl. The reaction mixture was extracted with ether. The organic phase was dried over MgSO$_4$, filtered and concentrated to obtain a colorless oil, which was then purified by BIOTAGE™ flash chromatography purification system, eluting with 0-25% EtOAc/hexane to isolate 3.1 g (61%) of tert-butyl 4-(allyloxy)-4-methylpiperidine-1-carboxylate as a colorless oil. $^1$H NMR (500 MHz, CDCl$_3$) δ 6.02-5.90 (m, 1H), 5.32 (dd, J=17.2, 1.7 Hz, 1H), 5.16 (dd, J=10.4, 1.4 Hz, 1H), 3.94-3.88 (m, 2H), 3.73 (br. s., 2H), 3.19 (br. s., 2H), 1.78 (d, J=13.1 Hz, 2H), 1.53-1.42 (m, 11H), 1.21 (s, 3H).

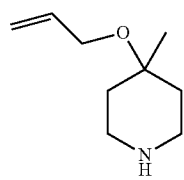

4-(Allyloxy)-4-methylpiperidine hydrochloride

A mixture of tert-butyl 4-(allyloxy)-4-methylpiperidine-1-carboxylate (3.10 g, 12.1 mmol) and 4N HCl/dioxane (15 mL, 60.0 mmol) was stirred at rt for 3 h. It was then concentrated in vacuum to obtain 2.2 g (95%) of 4-(allyloxy)-4-methylpiperidine hydrochloride as a light brown solid. $^1$H NMR (500 MHz, METHANOL-d$_4$) δ 6.02-5.92 (m, 1H), 5.33 (dd, J=17.2, 1.7 Hz, 1H), 5.15 (dd, J=10.6, 1.7 Hz, 1H), 3.96 (dt, J=5.1, 1.6 Hz, 2H), 3.23-3.18 (m, 4H), 2.06 (dd, J=15.3, 2.5 Hz, 2H), 1.77-1.69 (m, 2H), 1.31-1.28 (s, 3H).

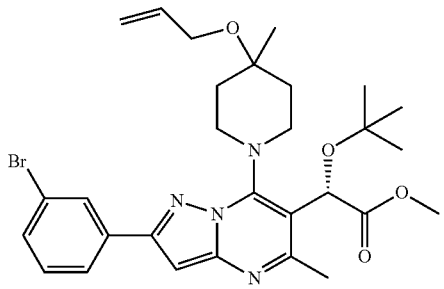 [SMILES: C=CCOC1(C)CCN(c2c([C@H](OC(C)(C)C)C(=O)OC)c(C)nc3cc(-c4cccc(Br)c4)nn23)CC1]

(S)-Methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (S)-methyl 2-(2-(3-bromophenyl)-7-chloro-5-methylpyrazolo[1,5-a]pyrimidin-6-yl)-2-(tert-butoxy)acetate (10.9 g, 23.3 mmol) was dissolved in DMF (100 mL). After flushing with N$_2$, 4-(allyloxy)-4-methylpiperidine.HCl (7.34 g, 35.0 mmol) and Hunig's Base (12.22 mL, 70.0 mmol) were added to the reaction mixture. After stirring for 18 h at rt, the reaction was heated at 50° C. for 3 h to complete the reaction. The reaction mixture was concentrated in vacuo at 50° C. to remove most of the DMF. The residue was partitioned between EtOAc and 0.01N HCl. The organic phase was washed with water and brine. Then, the organic phase was dried (MgSO$_4$), filtered, and concentrated in vacuo. The residue was dissolved in about 600 mL of hot hexanes and cooled for 18 h in the freezer to give a crystalline solid. Filtration gave 6.5 g of (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate. The filtrate was purified by BIOTAGE™ flash chromatography purification system (10-50% EtOAc) to give another 5.71 g of (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate. The combined yield of the desired product was 12.21 g (89%). $^1$H NMR (400 MHz, METHANOL-d$_4$) δ 8.23 (t, J=1.8 Hz, 1H), 8.01 (dt, J=7.8, 1.3 Hz, 1H), 7.60-7.55 (m, 1H), 7.43-7.37 (m, 1H), 6.90 (s, 1H), 6.18-5.95 (m, 2H), 5.48 (d, J=17.3 Hz, 1H), 5.25 (d, J=10.0 Hz, 1H), 4.11-4.06 (m, 2H), 3.77 (s, 3H), 2.59 (s, 3H), 2.14-1.95 (m, 3H), 1.82-1.71 (m, 1H), 1.37 (s, 3H), 1.28 (s, 9H). LCMS (M+H)=585 and 587.

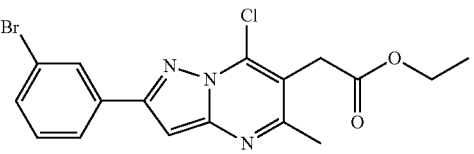 [SMILES: CCOC(=O)Cc1c(C)nc2cc(-c3cccc(Br)c3)nn2c1Cl]

Ethyl 2-(2-(3-bromophenyl)-7-chloro-5-methylpyrazolo[1,5-a]pyrimidin-6-yl)acetate Prepared according to the procedure for intermediate 4. $^1$H NMR (500 MHz, CDCl$_3$) δ 8.20 (t, J=1.7 Hz, 1H), 7.95 (qd, J=0.8, 7.8 Hz, 1H), 7.56 (ddd, J=1.0, 2.0, 8.0 Hz, 1H), 7.36 (t, J=7.9 Hz, 1H), 6.94 (s, 1H), 4.25 (q, J=7.1 Hz, 2H), 3.93 (s, 2H), 2.65 (s, 3H), 1.32 (t, J=7.1 Hz, 3H).

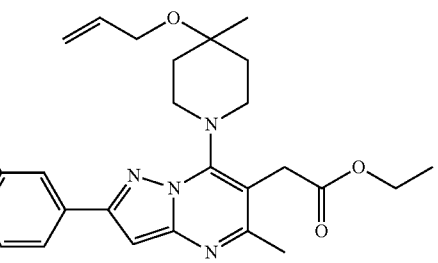

Ethyl 2-(7-(4-(allyloxy)-4-methylpiperidin-1-yl)-2-(3-bromophenyl)-5-methylpyrazolo[1,5-a]pyrimidin-6-yl)acetate A mixture of ethyl 2-(2-(3-bromophenyl)-7-chloro-5-methylpyrazolo[1,5-a]pyrimidin-6-yl)acetate (28 g, 68.5 mmol) in DMF (150 ml) was treated with 4-(allyloxy)-4-methylpiperidine.HCl (14.3 g, 74.6 mmol) and Hunig's Base (35.9 ml, 206 mmol), and the mixture was heated (60° C. oil bath) for 16 h. At this point LCMS indicates completion of reaction. Mixture was then cooled, diluted with Et$_2$O and washed with water (3×100 mL) and brine (100 mL), then dried (Na$_2$SO$_4$), filtered, and concentrated under reduced pressure. The residue was then purified by BIOTAGE™ flash chromatography purification system (5-50% EtOAc/hexane) to afford ethyl 2-(7-(4-(allyloxy)-4- methylpiperidin-1-yl)-2-(3-bromophenyl)-5-methylpyrazolo[1,5-a]pyrimidin-6-yl)acetate (32.6 g, 61.8 mmol, 90% yield) as viscous oil. ¹H NMR (500 MHz, CDCl₃) δ 8.16 (t, J=1.7 Hz, 1H), 7.94 (dt, J=7.8, 1.3 Hz, 1H), 7.54-7.49 (m, 1H), 7.37-7.30 (m, 1H), 6.79 (s, 1H), 6.13-5.99 (m, 1H), 5.51-5.40 (m, 1H), 5.26 (dd, J=10.4, 1.4 Hz, 1H), 4.24 (q, J=7.1 Hz, 2H), 4.03 (dt, J=5.2, 1.6 Hz, 2H), 3.82 (br. s, 4H), 3.32 (br. s., 2H), 2.54 (s, 3H), 1.99 (d, J=13.2 Hz, 2H), 1.86 (br. s., 2H), 1.36 (s, 3H), 1.31 (t, J=7.1 Hz, 3H). LCMS (M+H)=528.8.

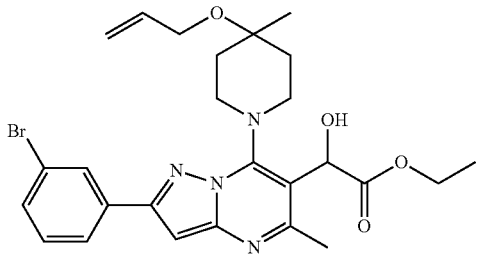 [SMILES: C=CCOC1(C)CCN(c2c(C(O)C(=O)OCC)c(C)nc3cc(-c4cccc(Br)c4)nn23)CC1]

Ethyl 2-(7-(4-(allyloxy)-4-methylpiperidin-1-yl)-2-(3-bromophenyl)-5-methylpyrazolo[1,5-a]pyrimidin-6-yl)-2-hydroxyacetate To a stirred solution of 1M KHMDS/THF (49.3 mL, 49.3 mmol) in THF (150 mL) at −78° C. was added dropwise a THF (100 mL) solution of ethyl 2-(7-(4-(allyloxy)-4-methylpiperidin-1-yl)-2-(3-bromophenyl)-5-methylpyrazolo[1,5-a]pyrimidin-6-yl)acetate (20 g, 37.9 mmol) over 5 min. After 30 min, a THF (100 mL) solution of 3-phenyl-2-(phenylsulfonyl)-1,2-oxaziridine (12.88 g, 49.3 mmol) was added and stirred for additional 30 min at −78° C. Then, the resulting dark reaction mixture was quenched with sat. NH₄Cl (50 mL), diluted with EtOAc (200 mL), washed with water (100 mL), brine (100 mL), dried (Na₂SO₄), filtered and concentrated. The residue was then purified by BIOTAGE™ flash chromatography purification system (5-50% EtOAc/hexane) to afford ethyl 2-(7-(4-(allyloxy)-4-methylpiperidin-1-yl)-2-(3-bromophenyl)-5-methylpyrazolo[1,5-a]pyrimidin-6-yl)-2-hydroxyacetate (17 g, 31.3 mmol, 82% yield) as white foam. Impurities were present by NMR. Used as is in the next step without further purification. ¹H NMR (500 MHz, CDCl₃) δ 8.16 (t, J=1.7 Hz, 1H), 7.99-7.92 (m, 1H), 7.58-7.50 (m, 2H), 7.34 (t, J=7.9 Hz, 1H), 6.83 (s, 1H), 6.18-6.06 (m, 1H), 5.57 (d, J=5.4 Hz, 1H), 5.48 (d, J=17.0 Hz, 1H), 5.27 (d, J=10.2 Hz, 1H), 4.83 (br. s., 2H), 4.35 (dq, J=10.8, 7.1 Hz, 1H), 4.23 (dq, J=10.9, 7.1 Hz, 1H), 4.06-3.99 (m, 2H), 2.65 (s, 3H), 2.00 (d, J=14.2 Hz, 2H), 1.84 (d, J=13.4 Hz, 2H), 1.36 (s, 3H), 1.29-1.26 (m, 3H). LCMS (M+H)=545.3.

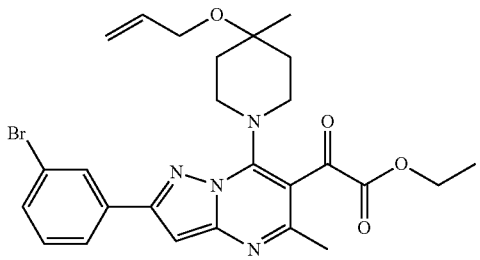 [SMILES: C=CCOC1(C)CCN(c2c(C(=O)C(=O)OCC)c(C)nc3cc(-c4cccc(Br)c4)nn23)CC1]

Ethyl 2-(7-(4-(allyloxy)-4-methylpiperidin-1-yl)-2-(3-bromophenyl)-5-methylpyrazolo[1,5-a]pyrimidin-6-yl)-2-oxoacetate To a solution of ethyl 2-(7-(4-(allyloxy)-4-methylpiperidin-1-yl)-2-(3-bromophenyl)-5-methylpyrazolo[1,5-a]pyrimidin-6-yl)-2-hydroxyacetate (32 g, 58.9 mmol) in dry DCM (500 mL) was added Dess-Martin periodinane (24.97 g, 58.9 mmol). The resulting bright orange-red solution was stirred for 90 min. The reaction was quenched by stirring with a saturated solution of Na₂S₂O₃ (100 mL) and sat. NaHCO₃ (100 mL) for 25 min to quench any unreacted Dess-Martin reagent. The reaction mixture was poured into a separatory funnel and organic layer separated. The aqueous layer was further extracted with EtOAc. The two organic components were separately washed with brine, then combined, dried (Na₂SO₄), filtered, and concentrated under reduced pressure. The residue was then purified via BIOTAGE™ flash chromatography purification system (5-40%) EtOAc/hexane to afford ethyl 2-(7-(4-(allyloxy)-4-methylpiperidin-1-yl)-2-(3-bromophenyl)-5-methylpyrazolo[1,5-a]pyrimidin-6-yl)-2-oxoacetate (22.6 g, 41.7 mmol, 70.9% yield) as off-white solid. ¹H NMR (500 MHz, CDCl₃) δ 8.12 (t, J=1.7 Hz, 1H), 7.91 (dt, J=7.8, 1.3 Hz, 1H), 7.56 (ddd, J=8.0, 2.0, 0.9 Hz, 1H), 7.37 (t, J=7.9 Hz, 1H), 6.82 (s, 1H), 6.00 (ddt, J=17.2, 10.4, 5.2 Hz, 1H), 5.44-5.36 (m, 1H), 5.24-5.17 (m, 1H), 4.46-4.35 (m, 2H), 3.98 (dt, J=5.1, 1.5 Hz, 2H), 3.80-3.71 (m, 2H), 3.69-3.60 (m, 2H), 2.60 (s, 3H), 2.03-1.88 (m, 4H), 1.46-1.40 (m, 3H), 1.31 (s, 3H). LCMS (M+H)=543.3.

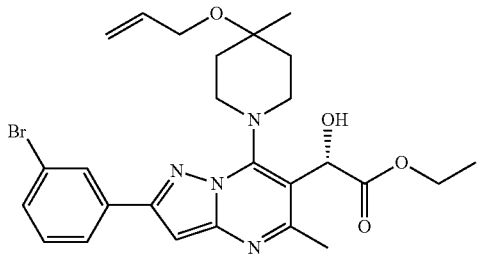 [SMILES: C=CCOC1(C)CCN(c2c([C@H](O)C(=O)OCC)c(C)nc3cc(-c4cccc(Br)c4)nn23)CC1]

(S)-Ethyl 2-(7-(4-(allyloxy)-4-methylpiperidin-1-yl)-2-(3-bromophenyl)-5-methylpyrazolo[1,5-a]pyrimidin-6-yl)-2-hydroxyacetate To a stirred yellow solution of ethyl 2-(7-(4-(allyloxy)-4-methylpiperidin-1-yl)-2-(3-bromophenyl)-5-methylpyrazolo[1,5-a]pyrimidin-6-yl)-2-oxoacetate (22 g, 40.6 mmol) in anhydrous toluene (800 mL) was added 1M (R)-1-methyl-3,3-diphenylhexahydropyrrolo[1,2-c][1,3,2]oxazaborole/toluene (16.25 mL, 16.25 mmol). The mixture was cooled to −35° C. and catechoborane (7.11 mL, 56.9 mmol) was added over 5 min. After 30 min, the reaction mixture was slowly warmed to −15° C. and stirred for additional 2 h. A this point LCMS indicated approx 60% conversion, so mixture was cooled to −35° C. and 3.5 mL of catechoborane was added and stirred at −15° C. for 2 h. At his point LCMS indicates completion of reaction. Mixture was then diluted with EtOAc (1 L) and sat. Na₂CO₃ (300 mL). The mixture was stirred vigorously for 30 min, and the organic phase washed with sat Na₂CO₃ (2×200 mL) each time vigorously stirring for 30 min, dried (Na₂SO₄), filtered, concentrated and the residue was purified by silica gel chromatography (5-70% EtOAc/hexane) to afford desired (S)-ethyl 2-(7-(4-(allyloxy)-4-methylpiperidin-1-yl)-2-(3-bromophenyl)-5-methylpyrazolo[1,5-a]pyrimidin-6-yl)-2-hydroxyacetate (17 g, 31.3 mmol, 77% yield) as off-white solid. ¹H NMR (500

MHz, CDCl₃) δ 8.19-8.10 (m, 1H), 7.95 (d, J=7.9 Hz, 1H), 7.58-7.52 (m, 1H), 7.33 (t, J=7.8 Hz, 1H), 6.86-6.82 (m, 1H), 6.10 (dd, J=10.8, 5.1 Hz, 1H), 5.57 (d, J=5.2 Hz, 1H), 5.48 (d, J=16.9 Hz, 1H), 5.27 (d, J=10.2 Hz, 1H), 4.35 (dq, J=10.8, 7.2 Hz, 1H), 4.23 (dq, J=10.7, 7.1 Hz, 1H), 4.03 (dt, J=5.2, 1.5 Hz, 2H), 2.65 (s, 3H), 2.00 (d, J=14.5 Hz, 2H), 1.84 (br. s., 2H), 1.36 (s, 3H), 1.29-1.24 (m, 3H). LCMS (M+H)=543.4.

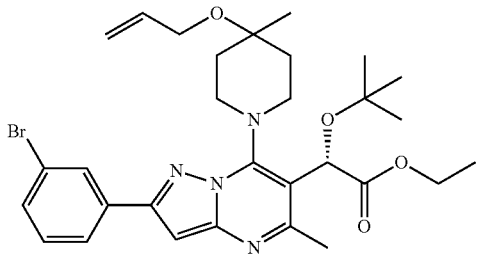 [SMILES: C=CCOC1(C)CCN(c2c([C@H](OC(C)(C)C)C(=O)OCC)c(C)nc3cc(-c4cccc(Br)c4)nn23)CC1]

(S)-Ethyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate To a stirred solution of (S)-ethyl 2-(7-(4-(allyloxy)-4-methylpiperidin-1-yl)-2-(3-bromophenyl)-5-methylpyrazolo[1,5-a]pyrimidin-6-yl)-2-hydroxyacetate (8.5 g, 15.64 mmol) in DCM (250 mL) and t-butyl acetate (175 mL) was added perchloric acid (4.03 mL, 46.9 mmol) at rt. After 3 h, the reaction mixture was diluted with DCM (100 mL), carefully quenched with sat. NaHCO₃ (50 mL), organic layer separated and washed with brine (100 mL), dried (Na₂SO₄), filtered and concentrated to give yellow liquid. This was purified by flash column chromatography on silica gel column using (10-50% EtOAc/Hex as eluant) to afford the desired (S)-ethyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (5 g, 8.34 mmol, 53.3% yield) as light yellow solid. 3 g of starting material was also recovered. ¹H NMR (500 MHz, CDCl₃) δ 8.23-8.11 (m, 1H), 7.94 (d, J=7.7 Hz, 1H), 7.56-7.51 (m, 1H), 7.33 (t, J=7.9 Hz, 1H), 6.81 (s, 1H), 6.10 (br. s., 1H), 6.00 (br. s., 1H), 5.49 (d, J=16.6 Hz, 1H), 5.28 (d, J=10.2 Hz, 1H), 4.30-4.14 (m, 2H), 4.10-4.00 (m, 2H), 2.65 (s, 3H), 2.09-1.85 (m, 3H), 1.74 (br. s., 1H), 1.38 (s, 3H), 1.28-1.16 (m, 12H). 4 missing piperidine hydrogens. LCMS (M+H)=601.5.

Synthesis of intermediate (S)-methyl 2-(tert-butoxy)-2-(2-(4'-fluoro-2'-hydroxy-[1,1'-biphenyl]-3-yl)-7-(4-hydroxyphenyl)-5-methylpyrazolo[1,5-a]pyrimidin-6-yl)acetate

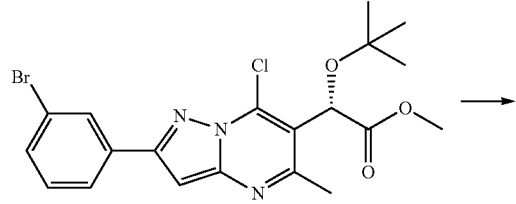

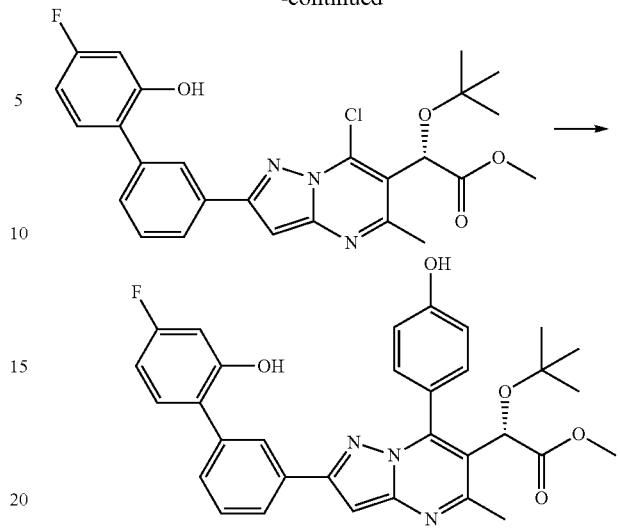

Step 1: A mixture of (S)-methyl 2-(2-(3-bromophenyl)-7-chloro-5-methylpyrazolo[1,5-a]pyrimidin-6-yl)-2-(tert-butoxy)acetate (300 mg, 0.643 mmol), (4-fluoro-2-hydroxyphenyl)boronic acid (110 mg), K₂CO₃ (178 mg) and [1,1'-bis(diphenylphosphino)ferrocene]dichloropalladium(II) (47.0 mg) in dioxane (8 mL)/water (1.6 mL) was heated at 85° C. in a sealed tube for 4 hours. The mixture was diluted with EtOAc (20 mL), washed with water (20 mL), brine (20 mL), dried over MgSO₄ and concentrated under vacuum. The residue was purified by silica gel column (hexanes/EtOAc=4:1) to give (S)-methyl 2-(tert-butoxy)-2-(7-chloro-2-(4'-fluoro-2'-hydroxy-[1,1'-biphenyl]-3-yl)-5-methylpyrazolo[1,5-a]pyrimidin-6-yl)acetate (200 mg). LCMS: MS (M+H)⁺ calcd. 498.2; observ. 498.3.

Step 2: To a mixture of(S)-methyl 2-(tert-butoxy)-2-(7-chloro-2-(4'-fluoro-2'-hydroxy-[1,1'-biphenyl]-3-yl)-5-methylpyrazolo[1,5-a]pyrimidin-6-yl)acetate (70 mg), 4-hydroxyphenylboronic acid (23.27 mg) and NaHCO₃ (35.4 mg) in dioxane (3 mL)/water (0.75 mL) was added Pd(PPh₃)₄ (16.24 mg) in a sealed tube. The mixture was heated at 90° C. for 3 hours. The mixture was diluted with EtOAc (20 mL), washed with water (20 mL), brine (20 mL), dried over MgSO₄ and concentrated under vacuum. The residue was purified by silica gel column (hexane/EtOAc=2:1) to give (S)-methyl 2-(tert-butoxy)-2-(2-(4'-fluoro-2'-hydroxy-[1,1'-biphenyl]-3-yl)-7-(4-hydroxyphenyl)-5-methylpyrazolo[1,5-a]pyrimidin-6-yl)acetate (50 mg). LCMS: MS (M+H)⁺ calcd. 556.2; observ. 555.9.

General procedure to synthesize macrocyclic structures from (S)-methyl 2-(tert-butoxy)-2-(2-(4'-fluoro-2'-hydroxy-[1,1'-biphenyl]-3-yl)-7-(4-hydroxyphenyl)-5-methylpyrazolo[1,5-a]pyrimidin-6-yl)acetate

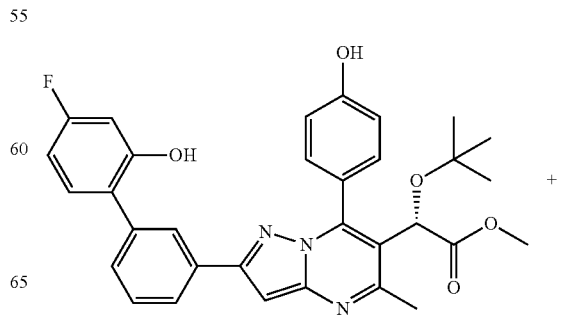

-continued

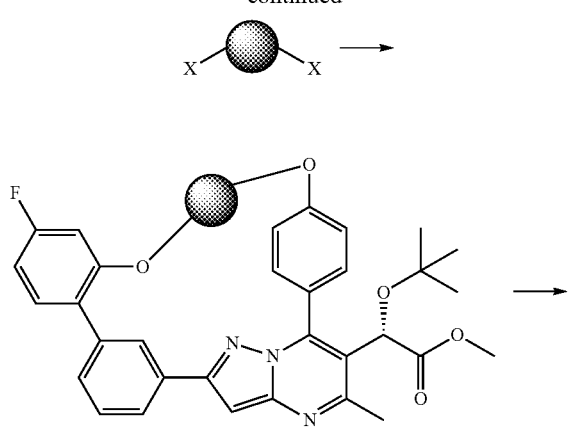

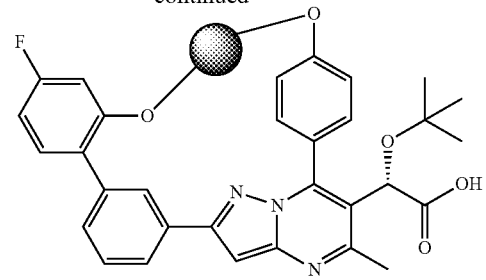

Step 1: To a solution of (S)-methyl 2-(tert-butoxy)-2-(2-(4'-fluoro-2'-hydroxy-[1,1'-biphenyl]-3-yl)-7-(4-hydroxyphenyl)-5-methylpyrazolo[1,5-a]pyrimidin-6-yl)acetate (1 eq.) and an electrophile (1.5 eq.) in DMF was added $Cs_2CO_3$ (2-10 eq.). The mixture was stirred at room temperature for 6-48 hours. After the solvent was removed under vacuum, the residue was purified by preparative HPLC to give a desired macrocyclic ester.

| Name | X⚬X | Intermediate | LCMS (M + H) |
|---|---|---|---|
| Methyl (2S)-2-(tert-butoxy)-2-{18-fluoro-4-methyl-21,28-dioxa-5,7,8-triazahexacyclo [27.2.2.1$^{6,9}$.1$^{10,14}$.0$^{2,7}$.0$^{15,20}$] pentatriaconta-1(31),2,4,6(35),8,10(34),11,13,15(20),16,18,29,32-tridecaen-3-yl}acetate | I⁀⁀⁀⁀⁀⁀I | 19 | 638.0 |

Step 2: To a solution of a macrocyclic ester obtained in step 1 (1 eq.) in MeOH/THF/water (volume ratio 2:1:1) was added NaOH (20 eq.). The mixture was stirred at room temperature for 4 hours. The mixture was acidified by 1N HCl to pH ~4. All the solvents were removed under vacuum. The residue was purified by preparative HPLC to give a desired macrocyclic acid.

| Name | X⚬X | Example | LCMS (M + H) |
|---|---|---|---|
| (2S)-2-(tert-butoxy)-2-{18-fluoro-4-methyl-21,28-dioxa-5,7,8-triazahexacyclo [27.2.2.1$^{6,9}$.1$^{10,14}$.0$^{2,7}$.0$^{15,20}$] pentatriaconta-1(31),2,4,6(35),8,10(34),11,13,15(20),16,18,29,32-tridecaen-3-yl}acetic acid | I⁀⁀⁀⁀⁀⁀I | 1 | 624.0 |

| Name | X⬤X | Example | LCMS (M + H) |
|---|---|---|---|
| (2S)-2-(tert-butoxy)-2-[(23E)-18-fluoro-4-methyl-21,26-dioxa-5,7,8-triazahexacyclo[25.2.1$^{6,9}$.1$^{10,14}$.0$^{2,7}$.0$^{15,20}$]tritriaconta-1(29),2,4,6(33),8,10(32),11,13,15(20),16,18,23,27,30-tetradecaen-3-yl]acetic acid |  | <br>2 | 594.2 |
| (2S)-2-(tert-butoxy)-2-{18-fluoro-4-methyl-21,29-dioxa-5,7,8-triazaheptacyclo[28.2.2.1$^{6,9}$.1$^{10,14}$.1$^{23,27}$.0$^{2,7}$.0$^{15,20}$]heptatriaconta-1(32),2,4,6(37),8,10(36),11,13,15(20),16,18,23(35),24,26,30,33-hexadecaen-3-yl}acetic acid | 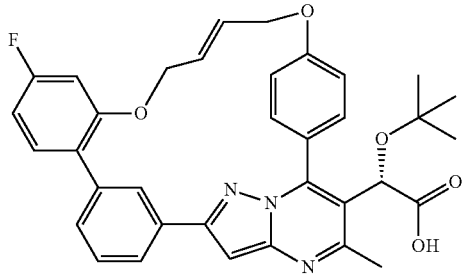 | 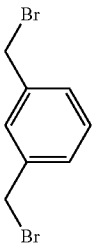<br>3 | 644.3 |
| (2S)-2-(tert-butoxy)-2-{18-fluoro-4-methyl-21,26-dioxa-5,7,8-triazahexacyclo[25.2.1$^{6,9}$.1$^{10,14}$.0$^{2,7}$.0$^{15,20}$]tritriaconta-1(29),2,4,6(33),8,10(32),11,13,15(20),16,18,27,30-tridecaen-23-yn-3-yl}acetic acid | 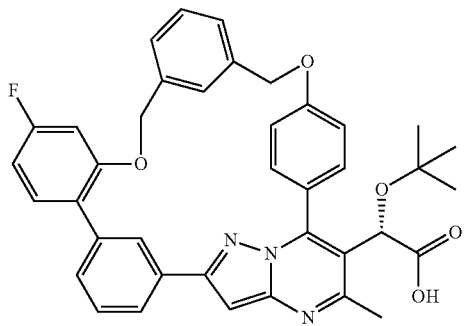 | <br>4 | 592.2 |
| (2S)-2-(tert-butoxy)-2-{18-fluoro-4-methyl-21,24,27-trioxa-5,7,8-triazahexacyclo[26.2.1$^{6,9}$.1$^{10,14}$.0$^{2,7}$.0$^{15,20}$]tetratriaconta-1(30),2,4,6(34),8,10(33),11,13,15(20),16,18,28,31-tridecaen-3-yl}acetic acid | 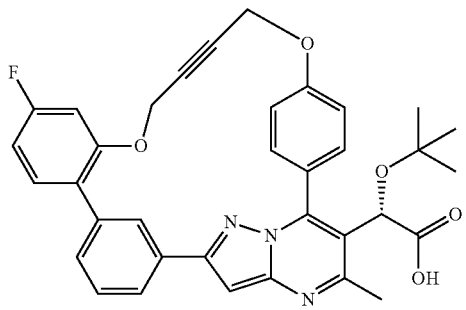 | 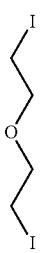<br>5 | 612.2 |

Synthesis of Intermediate (2S)-methyl 2-(tert-butoxy)-2-(2-(4'-fluoro-2'-hydroxy-[1,1'-biphenyl]-3-yl)-7-(4-hydroxynaphthalen-1-yl)-5-methylpyrazolo[1,5-a]pyrimidin-6-yl)acetate

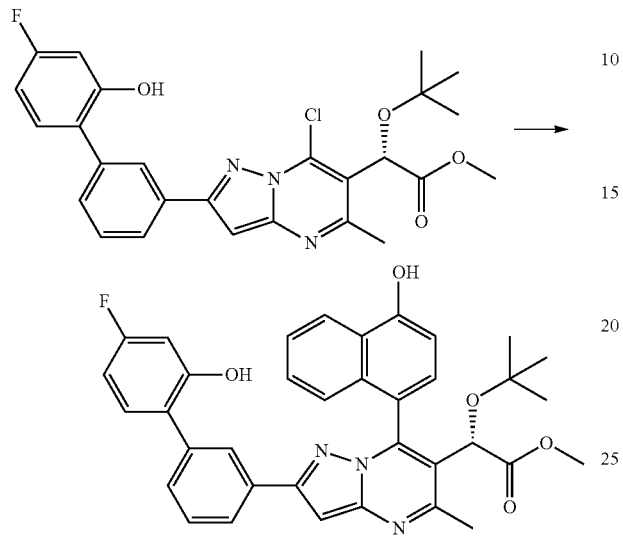

To a mixture of (S)-methyl 2-(tert-butoxy)-2-(7-chloro-2-(4'-fluoro-2'-hydroxy-[1,1'-biphenyl]-3-yl)-5-methylpyrazolo[1,5-a]pyrimidin-6-yl)acetate (90 mgl), 4-(4,4,5,5-tetramethyl-1,3,2-dioxaborolan-2-yl)naphthalen-1-ol (73.2 mg) and $Na_2CO_3$ (45.6 mg) in dioxane (5 mL) and water (1.25 mL) was added $Pd(PPh_3)_4$ (20.89 mg) in a sealed tube. The reaction mixture was heated at 90° C. for 24 hours. Then, the reaction mixture was diluted with EtOAc (20 mL), washed with water (2×10 mL), brine (10 mL), dried over $MgSO_4$ and concentrated under vacuum to give a residue which was purified by silica gel column (hexane/EtOAc=2:1) to give (2S)-methyl 2-(tert-butoxy)-2-(2-(4'-fluoro-2'-hydroxy-[1,1'-biphenyl]-3-yl)-7-(4-hydroxynaphthalen-1-yl)-5-methylpyrazolo[1,5-a]pyrimidin-6-yl)acetate (70 mg). LCMS (M+H)=606.4.

Synthesis of (2S)-2-(tert-butoxy)-2-{18-fluoro-4-methyl-21,29-dioxa-5,7,8-triazaoctacyclo[28.6.2.1$^{6,9}$.1$^{10,14}$.1$^{23,27}$.0$^{2,7}$.0$^{15,20}$.0$^{31,36}$]hentetraconta-1(37),2,4,6(41),8,10(40),11,13,15(20),16,18,23(39),24,26,30(38),31(36),32,34-octadecaen-3-yl}acetic acid

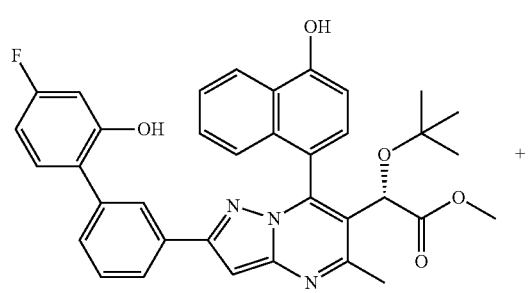

+

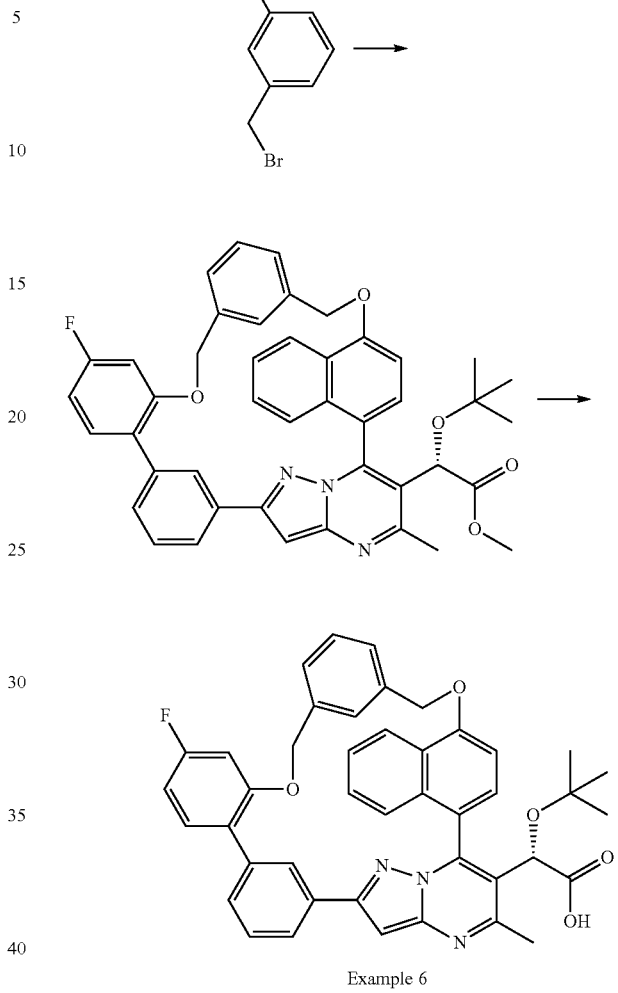

Example 6

Step 1: To a solution of (2S)-methyl 2-(tert-butoxy)-2-(2-(4'-fluoro-2'-hydroxy-[1,1'-biphenyl]-3-yl)-7-(4-hydroxynaphthalen-1-yl)-5-methylpyrazolo[1,5-a]pyrimidin-6-yl)acetate (1 eq.) and an electrophile (1.5 eq.) in DMF was added $Cs_2CO_3$ (2-10 eq.). The mixture was stirred at room temperature for 6-48 hours. After the solvent was removed under vacuum, the residue was purified by preparative HPLC to give a desired methyl (2S)-2-(tert-butoxy)-2-{18-fluoro-4-methyl-21,29-dioxa-5,7,8-triazaoctacyclo[28.6.2.1$^{6,9}$.1$^{10,14}$.1$^{23,27}$.0$^{2,7}$.0$^{15,20}$.0$^{31,36}$]hentetraconta-1(37),2,4,6(41),8,10(40),11,13,15(20),16,18,23(39),24,26,30(38),31(36),32,34-octadecaen-3-yl}acetate. LCMS (M+H)=708.3

Step 2: To a solution of a macrocyclic ester obtained in step 1 (1 eq.) in MeOH/THF/water (volume ratio 2:1:1) was added NaOH (20 eq.). The mixture was stirred at room temperature for 4 hours. The mixture was acidified by 1N HCl to pH ~4. All the solvents were removed under vacuum. The residue was purified by preparative HPLC to give a desired (2S)-2-(tert-butoxy)-2-{18-fluoro-4-methyl-21,29-dioxa-5,7,8-triazaoctacyclo[28.6.2.1$^{6,9}$.1$^{10,14}$.1$^{23,27}$.0$^{2,7}$.0$^{15,20}$.0$^{31,36}$]hentetraconta-1(37),2,4,6(41),8,10(40),11,13,15(20),16,18,23(39),24,26,30(38),31(36),32,34-octadecaen-3-yl}acetic acid. LCMS (M+H)=694.3.

Synthesis of (2S)-2-(tert-butoxy)-2-{18-fluoro-4-methyl-21,26-dioxa-5, 7, 8-triazaheptacyclo[25.6.2.1$^{6,9}$.1$^{10,14}$.0$^{2,7}$.0$^{15,20}$.0$^{28,33}$]heptatriaconta-1(34),2,4,6(37),8,10(36),11,13,15(20),16,18,27(35),28(33),29,31-pentadecaen-23-yn-3-yl}acetic acid

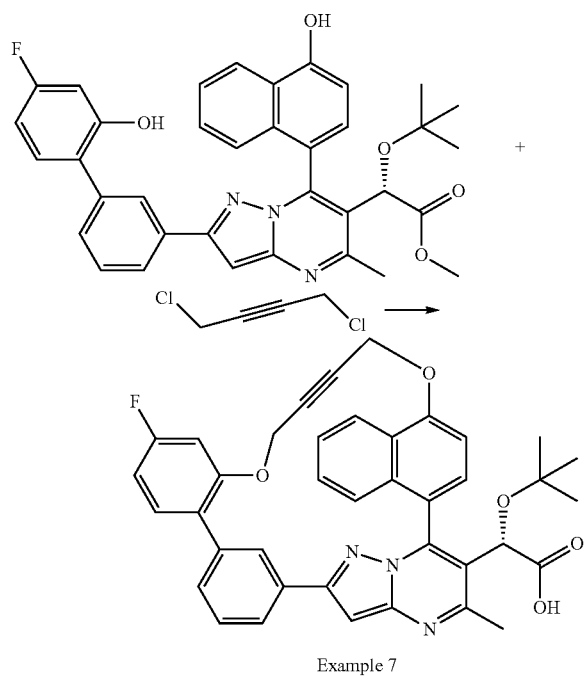

Example 7

To a solution of (2S)-methyl 2-(tert-butoxy)-2-(2-(4'-fluoro-2'-hydroxy-[1,1'-biphenyl]-3-yl)-7-(4-hydroxynaphthalen-1-yl)-5-methylpyrazolo[1,5-a]pyrimidin-6-yl)acetate (8 mg) and 1,4-dichloro-2-butyne (3.25 mg) in DMF (3 mL) was added cesium carbonate (17.21 mg). The reaction was stirred at room temperature for 48 hours. The solvent was removed under vacuum. The residue was diluted with MeOH (0.5 mL), THF (0.250 mL) and water (0.500 mL), before 1 mL of 1N NaOH was added. After the mixture was stirred at room temperature for 4 hours, it was acidified with 1N HCl to pH=3. All the solvents were removed under vacuum to give a residue which was purified by preparative HPLC to give (2S)-2-(tert-butoxy)-2-{18-fluoro-4-methyl-21,26-dioxa-5,7,8-triazaheptacyclo[25.6.2.1$^{6,9}$.1$^{10,14}$.0$^{2,7}$.0$^{15,20}$.0$^{28,33}$]heptatriaconta-1(34),2,4,6(37),8,10(36),11,13,15(20),16,18,27(35),28(33),29,31-pentadecaen-23-yn-3-yl)}acetic acid (0.55 mg). LCMS (M+H)=642.2.

Synthesis of intermediate (S)-ethyl 2-(tert-butoxy)-2-(2-(4'-fluoro-2'-hydroxy-[1,1'-biphenyl]-3-yl)-7-(3-hydroxy-4-methylphenyl)-5-methylpyrazolo[1,5-a]pyrimidin-6-yl)acetate

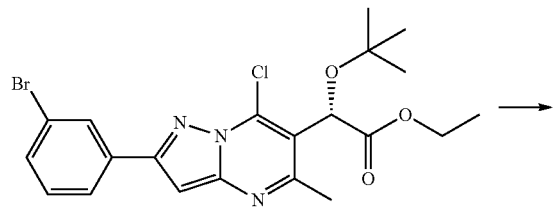

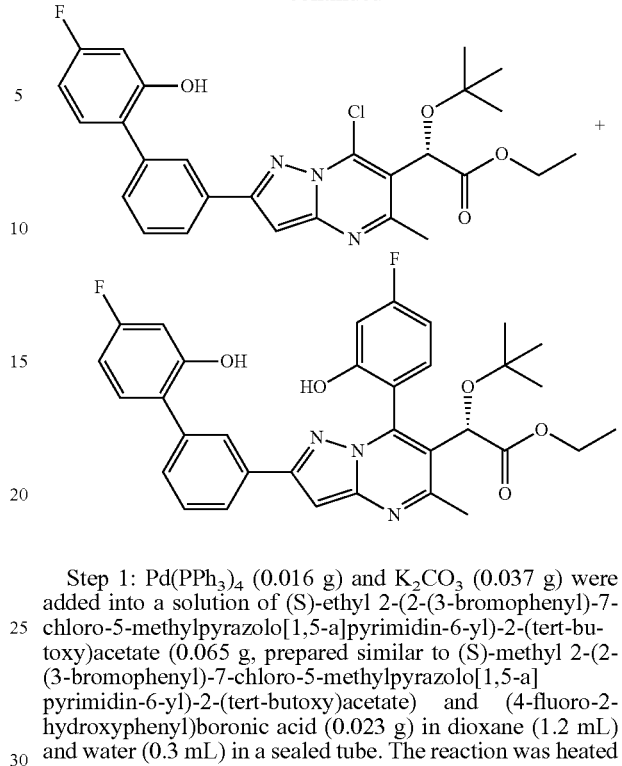

Step 1: Pd(PPh$_3$)$_4$ (0.016 g) and K$_2$CO$_3$ (0.037 g) were added into a solution of (S)-ethyl 2-(2-(3-bromophenyl)-7-chloro-5-methylpyrazolo[1,5-a]pyrimidin-6-yl)-2-(tert-butoxy)acetate (0.065 g, prepared similar to (S)-methyl 2-(2-(3-bromophenyl)-7-chloro-5-methylpyrazolo[1,5-a]pyrimidin-6-yl)-2-(tert-butoxy)acetate) and (4-fluoro-2-hydroxyphenyl)boronic acid (0.023 g) in dioxane (1.2 mL) and water (0.3 mL) in a sealed tube. The reaction was heated at 90° C. for 16 hours. After removal of solvents under vacuum, the residue was purified by preparative HPLC to afford (S)-ethyl 2-(tert-butoxy)-2-(7-chloro-2-(4'-fluoro-2'-hydroxy-[1,1'-biphenyl]-3-yl)-5-methylpyrazolo[1,5-a]pyrimidin-6-yl)acetate, LCMS: MS (M+H)$^+$ calcd. 512.2; observ. 512.1, and, (2S)-ethyl 2-(tert-butoxy)-2-(2-(4'-fluoro-2'-hydroxy-[1,1'-biphenyl]-3-yl)-7-(4-fluoro-2-hydroxyphenyl)-5-methylpyrazolo[1,5-a]pyrimidin-6-yl)acetate, LCMS (M+H)=588.2.

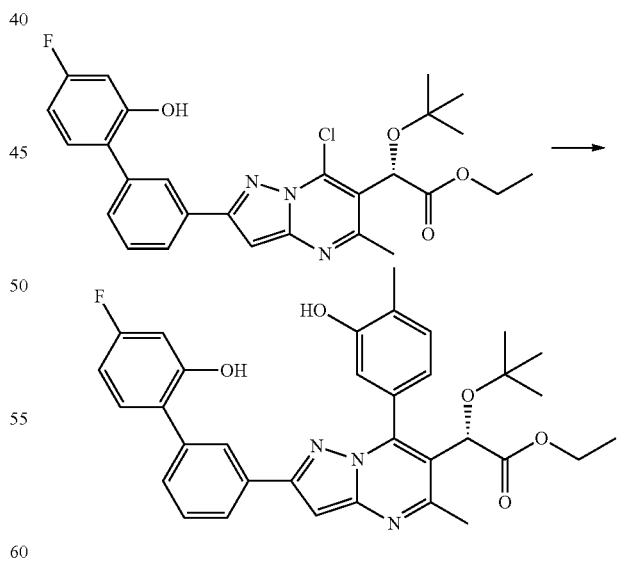

Step 2: Pd(PPh$_3$)$_4$ (0.032 g) and K$_2$CO$_3$ (0.076 g) were added into a solution of (S)-ethyl 2-(tert-butoxy)-2-(7-chloro-2-(4'-fluoro-2'-hydroxy-[1,1'-biphenyl]-3-yl)-5-methylpyrazolo[1,5-a]pyrimidin-6-yl)acetate (0.14 g) and (3-hydroxy-4-methylphenyl)boronic acid (0.046 g) in dioxane (5 mL) and water (1 mL) in a sealed tube. The reaction was heated at 85° C. for 2 hours. After removal of solvents under vacuum, the residue was purified by preparative HPLC to afford (S)-ethyl 2-(tert-butoxy)-2-(2-(4'-fluoro-2'-hydroxy-[1,1'-biphenyl]-3-yl)-7-(3-hydroxy-4-methylphenyl)-5-methylpyrazolo[1,5-a]pyrimidin-6-yl)acetate. LCMS: MS (M+H)+ calcd. 584.3; observ. 584.3.

General procedure to synthesize macrocyclic structures from (S)-ethyl 2-(tert-butoxy)-2-(2-(4'-fluoro-2'-hydroxy-[1,1'-biphenyl]-3-yl)-7-(3-hydroxy-4-methylphenyl)-5-methylpyrazolo[1,5-a]pyrimidin-6-yl)acetate

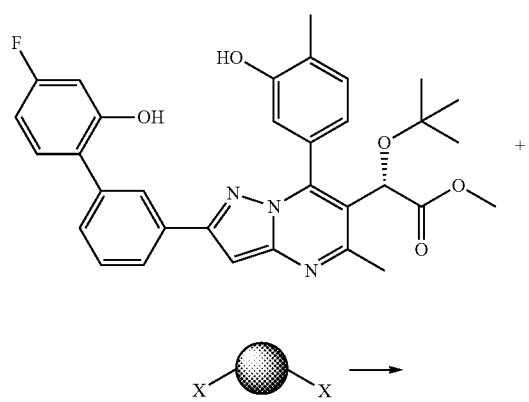

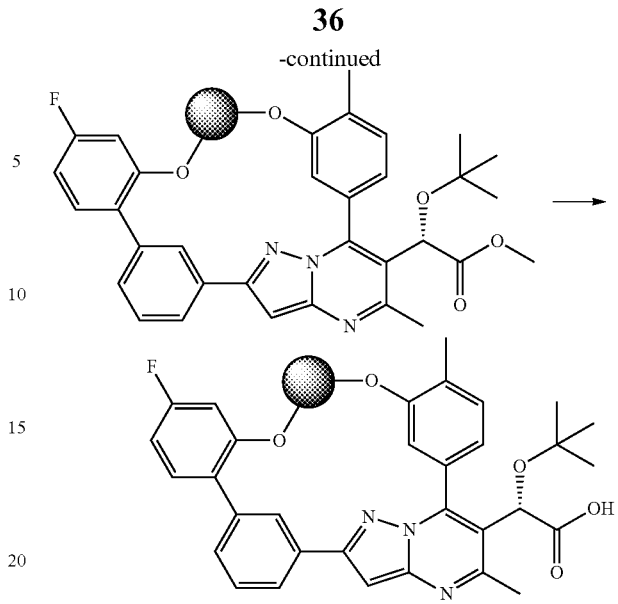

Step 1: $K_2CO_3$ (2-10 eq.) was added into a solution of (2S)-ethyl 2-(tert-butoxy)-2-(2-(4'-fluoro-2'-hydroxy-[1,1'-biphenyl]-3-yl)-7-(4-fluoro-2-hydroxyphenyl)-5-methylpyrazolo[1,5-a]pyrimidin-6-yl)acetate (1 eq.) and 3-chloro-2-(chloromethyl)prop-1-ene (1 eq.) in MeCN in a sealed tube. The reaction was heated at 85° C. for 16-48 hours. After removal of solvents under vacuum, the residue was purified by preparative HPLC to afford the desired macrocyclic ester.

| Name | X-●-X | Intermediate | LCMS (M + H) |
|---|---|---|---|
| Ethyl (2S)-2-(tert-butoxy)-2-{22-fluoro-7,13-dimethyl-17-methylidene-15,19-dioxa-3,4,6-triazahexacyclo[24.3.1.1$^{2,5}$.1$^{10,14}$.0$^{4,9}$.0$^{20,25}$]dotriaconta-1(30),2,5(32),6,8,10,12,14(31),20(25),21,23,26,28-tridecaen-8-yl}acetate | (structure with two Cl groups and methylidene) | (structure) | 636.3 |
| Ethyl (2S)-2-(tert-butoxy)-2-[(17E)-23-fluoro-7,13-dimethyl-15,20-dioxa-3,4,6-triazahexacyclo[25.3.1.1$^{2,5}$.1$^{10,14}$.0$^{4,9}$.0$^{21,26}$]tritriaconta-1(31),2,5(33),6,8,10,12,14(32),17,21(26),22,24,27,29-tetradecaen-8-yl]acetate | (structure with two Br groups and internal double bond) | (structure) | 636.3 |

| Name | X—⬤—X | Intermediate | LCMS (M + H) |
|---|---|---|---|
| Ethyl (2S)-2-(tert-butoxy)-2-{26-fluoro-7,13-dimethyl-15,23-dioxa-3,4,6,35-tetraazaheptacyclo[28.3.1.1$^{2,5}$.1$^{10,14}$.0$^{17,21}$.0$^{4,9}$.0$^{24,29}$]heptatriaconta-1(34),2,5(37),6,8,10,12,14(36),17(35),18,20,24(29),25,27,30,32-hexadecaen-8-yl}acetate | | | 687.0 |
| Ethyl (2S)-2-(tert-butoxy)-2-{18,18,19,19,25-pentafluoro-7,13-dimethyl-15,22-dioxa-3,4,6-triazahexacyclo[27.3.1.1$^{2,5}$.1$^{10,14}$.0$^{4,9}$.0$^{23,28}$]pentatriaconta-1(33),2,5(35),6,8,10,12,14(34),23(28),24,26,29,31-tridecaen-8-yl}acetate | | | 738.0 |
| Ethyl (2S)-2-(tert-butoxy)-2-{23-fluoro-7,13-dimethyl-15,20-dioxa-3,4,6-triazahexacyclo[25.3.1.1$^{2,5}$.1$^{10,14}$.0$^{4,9}$.0$^{21,26}$]tritriaconta-1(31),2,5(33),6,8,10,12,14(32),21(26),22,24,27,29-tridecaen-17-yn-8-yl}acetate | | | 634.0 |
| Ethyl (2S)-2-(tert-butoxy)-2-{18-tert-butyl-24-fluoro-7,13-dimethyl-15,21-dioxa-3,4,6,18-tetraazahexacyclo[26.3.1.1$^{2,5}$.1$^{10,14}$.0$^{4,9}$.0$^{22,27}$]tetratriaconta-1(32),2,5(34),6,8,10,12,14(33),22(27),23,25,28,30-tridecaen-8-yl}acetate | | | 709.5 |

| Name | X—●—X | Intermediate | LCMS (M + H) |
|---|---|---|---|
| Ethyl (2S)-2-(tert-butoxy)-2-{26-fluoro-7,13-dimethyl-15,23-dioxa-3,4,6-triazaheptacyclo[28.3.1.1²,⁵.1¹⁰,¹⁴.1¹⁷,²¹.0⁴,⁹.0²⁴,²⁹]heptatriaconta-1(34),2,5(37),6,8,10,12,14(36),17(35),18,20,24(29),25,27,30,32-hexadecaen-8-yl}acetate |  | 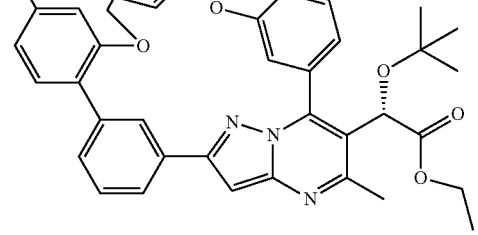 | 686.3 |
| Ethyl (2S)-2-(tert-butoxy)-2-{24-fluoro-7,13-dimethyl-15,18,21-trioxa-3,4,6-triazahexacyclo[26.3.1.1²,⁵.1¹⁰,¹⁴.0⁴,⁹.0²²,²⁷]tetratriaconta-1(32),2,5(34),6,8,10,12,14(33),22(27),23,25,28,30-tridecaen-8-yl}acetate | 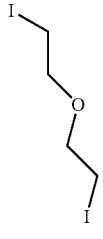 | 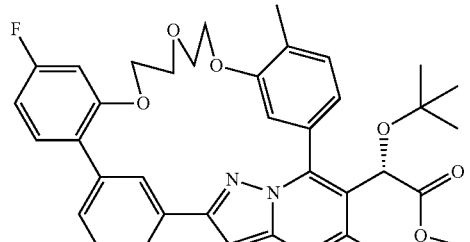 | 654.3 |
| Ethyl (2S)-2-(tert-butoxy)-2-{25-fluoro-7,13-dimethyl-15,22-dioxa-3,4,6-triazahexacyclo[27.3.1.1²,⁵.1¹⁰,¹⁴.0⁴,⁹.0²³,²⁸]pentatriaconta-1(33),2,5(35),6,8,10,12,14(34),23(28),24,26,29,31-tridecaen-8-yl}acetate | 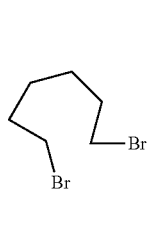 | 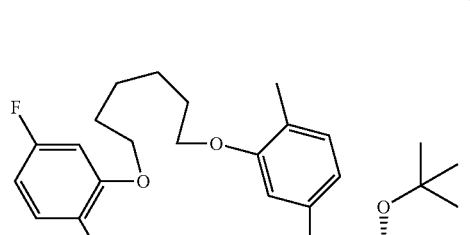 | 666.3 |
| Ethyl (2S)-2-{18-benzyl-24-fluoro-7,13-dimethyl-15,21-dioxa-3,4,6,18-tetraazahexacyclo[26.3.1.1²,⁵.1¹⁰,¹⁴.0⁴,⁹.0²²,²⁷]tetratriaconta-1(32),2,5(34),6,8,10,12,14(33),22(27),23,25,28,30-tridecaen-8-yl}-2-(tert-butoxy)acetate | 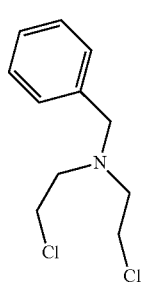 [SMILES: ClCCN(CCCl)Cc1ccccc1] | 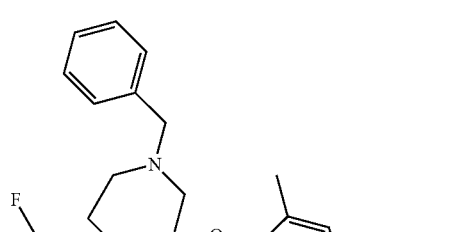 | 743.5 |

Step 2: NaOH (2-10 eq.) was added into a solution of macrocyclic ester obtained in step 1 (1 eq.) in methanol/THF/water (volume ratio 1:1:1) (0.5 mL). The reaction was stirred at room temperature for 1-24 hours. After removal of solvents under vacuum, the residue was purified by preparative HPLC to afford the desired macrocyclic acid.

| Name | Example | LCMS (M + H) |
|---|---|---|
| (2S)-2-(tert-Butoxy)-2-{22-fluoro-7,13-dimethyl-17-methylidene-15,19-dioxa-3,4,6-triazahexacyclo[24.3.1.1$^{2,5}$.1$^{10,14}$.0$^{4,9}$.0$^{20,25}$]dotriaconta-1(30),2,5(32),6,8,10,12,14(31),20(25),21,23,26,28-tridecaen-8-yl}acetic acid | 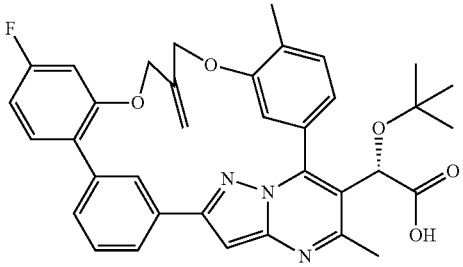<br>8 | 608.3 |
| (2S)-2-(tert-Butoxy)-2-[(17E)-23-fluoro-7,13-dimethyl-15,20-dioxa-3,4,6-triazahexacyclo[25.3.1.1$^{2,5}$.1$^{10,14}$.0$^{4,9}$.0$^{21,26}$]tritriaconta-1(31),2,5(33),6,8,10,12,14(32),17,21(26),22,24,27,29-tetradecaen-8-yl]acetic acid | 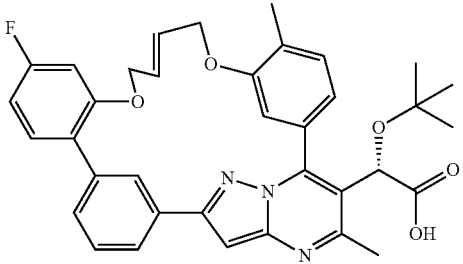<br>9 | 608.0 |
| (2S)-2-(tert-Butoxy)-2-{26-fluoro-7,13-dimethyl-15,23-dioxa-3,4,6,35-tetraazaheptacyclo[28.3.1.1$^{2,5}$.1$^{10,14}$.0$^{17,21}$.0$^{4,9}$.0$^{24,29}$]heptatriaconta-1(34),2,5(37),6,8,10,12,14(36),17(35),18,20,24(29),25,27,30,32-hexadecaen-8-yl}acetic acid | 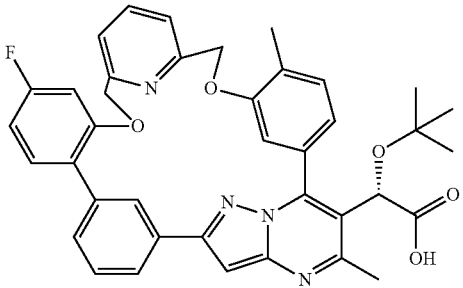<br>10 | 659.3 |
| (2S)-2-(tert-Butoxy)-2-[(17Z)-23-fluoro-7,13-dimethyl-15,20-dioxa-3,4,6-triazahexacyclo[25.3.1.1$^{2,5}$.1$^{10,14}$.0$^{4,9}$.0$^{21,26}$]tritriaconta-1(31),2,5(33),6,8,10,12,14(32),17,21(26),22,24,27,29-tetradecaen-8-yl]acetic acid | 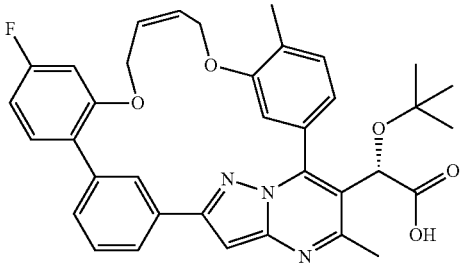<br>11 | 608.2 |

| Name | Example | LCMS (M + H) |
|---|---|---|
| (2S)-2-(tert-Butoxy)-2-{18,18,19,19,25-pentafluoro-7,13-dimethyl-15,22-dioxa-3,4,6-triazahexacyclo[27.3.1.1$^{2,5}$.1$^{10,14}$.0$^{4,9}$.0$^{23,28}$]pentatriaconta-1(33),2,5(35),6,8,10,12,14(34),23(28),24,26,29,31-tridecaen-8-yl}acetic acid | 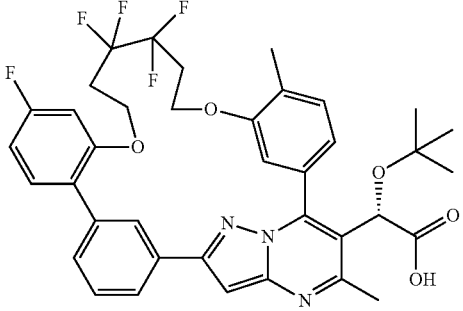 12 | 710.2 |
| (2S)-2-(tert-Butoxy)-2-{23-fluoro-7,13-dimethyl-15,20-dioxa-3,4,6-triazahexacyclo[25.3.1.1$^{2,5}$.1$^{10,14}$.0$^{4,9}$.0$^{21,26}$]tritriaconta-1(31),2,5(33),6,8,10,12,14(32),21(26),22,24,27,29-tridecaen-17-yn-8-yl}acetic acid | 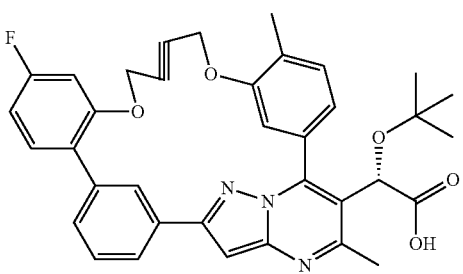 13 | 606.4 |
| (2S)-2-(tert-Butoxy)-2-{18-tert-butyl-24-fluoro-7,13-dimethyl-15,21-dioxa-3,4,6,18-tetraazahexacyclo[26.3.1.1$^{2,5}$.1$^{10,14}$.0$^{4,9}$.0$^{22,27}$]tetratriaconta-1(32),2,5(34),6,8,10,12,14(33),22(27),23,25,28,30-tridecaen-8-yl}acetic acid | 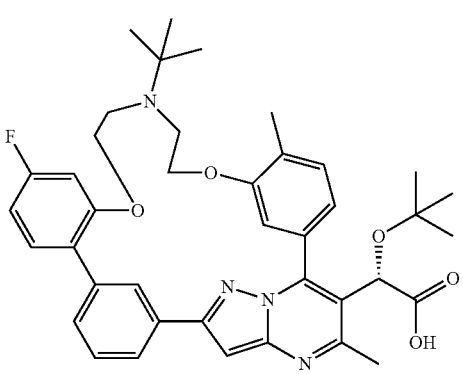 14 | 681.5 |
| (2S)-2-(tert-Butoxy)-2-{26-fluoro-7,13-dimethyl-15,23-dioxa-3,4,6-triazaheptacyclo[28.3.1.1$^{2,5}$.1$^{10,14}$.1$^{17,21}$.0$^{4,9}$.0$^{24,29}$]heptatriaconta-1(34),2,5(37),6,8,10,12,14(36),17(35),18,20,24(29),25,27,30,32-hexadecaen-8-yl}acetic acid | 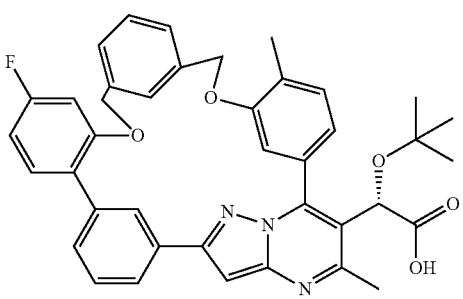 15 | 658.4 |

-continued

| Name | Example | LCMS (M + H) |
|---|---|---|
| (2S)-2-(tert-Butoxy)-2-{25-fluoro-7,13-dimethyl-15,22-dioxa-3,4,6-triazahexacyclo[27.3.1.1$^{2,5}$.1$^{10,14}$.0$^{4,9}$.0$^{23,28}$]pentatriaconta-1(33),2,5(35),6,8,10,12,14(34),23(28),24,26,29,31-tridecaen-8-yl}acetic acid | 16 | 638.3 |
| (2S)-2-(tert-Butoxy)-2-{24-fluoro-7,13-dimethyl-15,18,21-trioxa-3,4,6-triazahexacyclo[26.3.1.1$^{2,5}$.1$^{10,14}$.0$^{4,9}$.0$^{22,27}$]tetratriaconta-1(32),2,5(34),6,8,10,12,14(33),22(27),23,25,28,30-tridecaen-8-yl}acetic acid | 17 | 626.3 |
| (2S)-2-(tert-Butoxy)-2-{18-fluoro-4-methyl-21,29,33-trioxa-5,7,8-triazaoctacyclo[28.6.2.1$^{6,9}$.1$^{10,14}$.1$^{23,27}$.0$^{2,7}$.0$^{15,20}$.0$^{34,38}$]hentetraconta-1(36),2,4,6(41),8,10(40),11,13,15(20),16,18,23,25,27(39),34,37-hexadecaen-3-yl}acetic acid | 18 | 715.3 |

Synthesis of intermediate (2S)-ethyl 2-(tert-butoxy)-2-(2-(4'-fluoro-2'-hydroxy-[1,1'-biphenyl]-3-yl)-7-(4-fluoro-2-hydroxyphenyl)-5-methylpyrazolo[1,5-a]pyrimidin-6-yl)acetate -continued

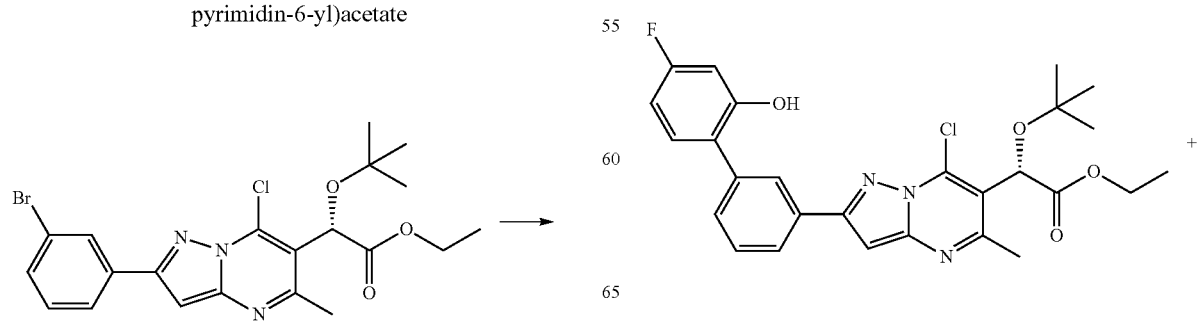

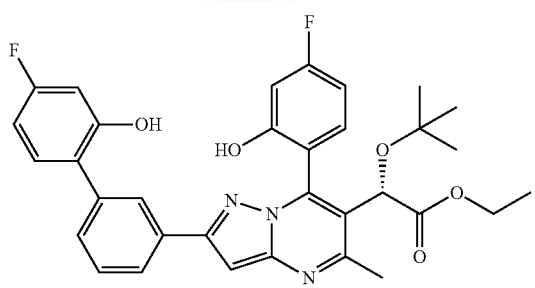
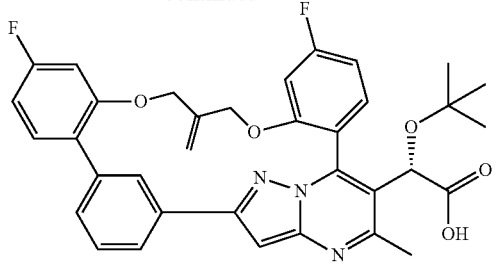

Example 19 (14)

Pd(PPh$_3$)$_4$ (0.016 g) and K$_2$CO$_3$ (0.037 g) were added into a solution of (S)-ethyl 2-(2-(3-bromophenyl)-7-chloro-5-methylpyrazolo[1,5-a]pyrimidin-6-yl)-2-(tert-butoxy)acetate (0.065 g) and (4-fluoro-2-hydroxyphenyl)boronic acid (0.023 g) in dioxane (1.2 mL) and water (0.3 mL) in a sealed tube. The reaction was heated at 90° C. for 16 hours. After removal of solvents under vacuum, the residue was purified by preparative HPLC to afford (S)-ethyl 2-(tert-butoxy)-2-(7-chloro-2-(4'-fluoro-2'-hydroxy-[1,1'-biphenyl]-3-yl)-5-methylpyrazolo[1,5-a]pyrimidin-6-yl)acetate, LCMS: MS (M+H)$^+$ calcd. 512.2; observ. 512.1, and, (2S)-ethyl 2-(tert-butoxy)-2-(2-(4'-fluoro-2'-hydroxy-[1,1'-biphenyl]-3-yl)-7-(4-fluoro-2-hydroxyphenyl)-5-methylpyrazolo[1,5-a]pyrimidin-6-yl)acetate, LCMS (M+H)=588.2.

General procedure to synthesize macrocyclic structures from (2S)-ethyl 2-(tert-butoxy)-2-(2-(4'-fluoro-2'-hydroxy-[1,1'-biphenyl]-3-yl)-7-(4-fluoro-2-hydroxyphenyl)-5-methylpyrazolo[1,5-a]pyrimidin-6-yl)acetate Step 1: K$_2$CO$_3$ (2-10 eq.) was added into a solution of (2S)-ethyl 2-(tert-butoxy)-2-(2-(4'-fluoro-2'-hydroxy-[1,1'-biphenyl]-3-yl)-7-(4-fluoro-2-hydroxyphenyl)-5-methylpyrazolo[1,5-a]pyrimidin-6-yl)acetate (1 eq.) and 3-chloro-2-(chloromethyl)prop-1-ene (1 eq.) in MeCN in a sealed tube. The reaction was heated at 85° C. for 16-48 hours. After removal of solvents under vacuum, the residue was purified by preparative HPLC to afford the desired ethyl (2S)-2-(tert-butoxy)-2-{13,23-difluoro-7-methyl-18-methylidene-16,20-dioxa-3,4,6-triazahexacyclo[25.3.1.1$^{2,5}$.0$^{4,9}$.0$^{10,15}$.0$^{21,26}$]dotriaconta-1(31),2,5(32),6,8,10,12,14,21(26),22,24,27,29-tridecaen-8-yl}acetate. LCMS (M+H)=640.1.

Step 2: NaOH (2-10 eq.) was added into a solution of macrocyclic ester obtained in step 1 (1 eq.) in methanol/THF/water (volume ratio 1:1:1) (0.5 mL). The reaction was stirred at room temperature for 1-24 hours. After removal of solvents under vacuum, the residue was purified by preparative HPLC to afford the desired (2S)-2-(tert-butoxy)-2-{13,23-difluoro-7-methyl-18-methylidene-16,20-dioxa-3,4,6-triazahexacyclo[25.3.1.1$^{2,5}$.0$^{4,9}$.0$^{10,15}$.0$^{21,26}$]dotriaconta-1(31),2,5(32),6,8,10,12,14,21(26),22,24,27,29-tridecaen-8-yl}acetic acid. LCMS (M+H)=612.4.

Synthesis of (2S)-2-(tert-butoxy)-2-{25-fluoro-7,13-dimethyl-16, 22-dioxa-3,4,6-triazahexacyclo[27.3.1.1$^{2,5}$.0$^{4,9}$.0$^{10,15}$.0$^{23,28}$]tetratriaconta-1(33),2,5(34),6,8,10,12,14, 23(28),24,26,29,31-tridecaen-8-yl}acetic acid

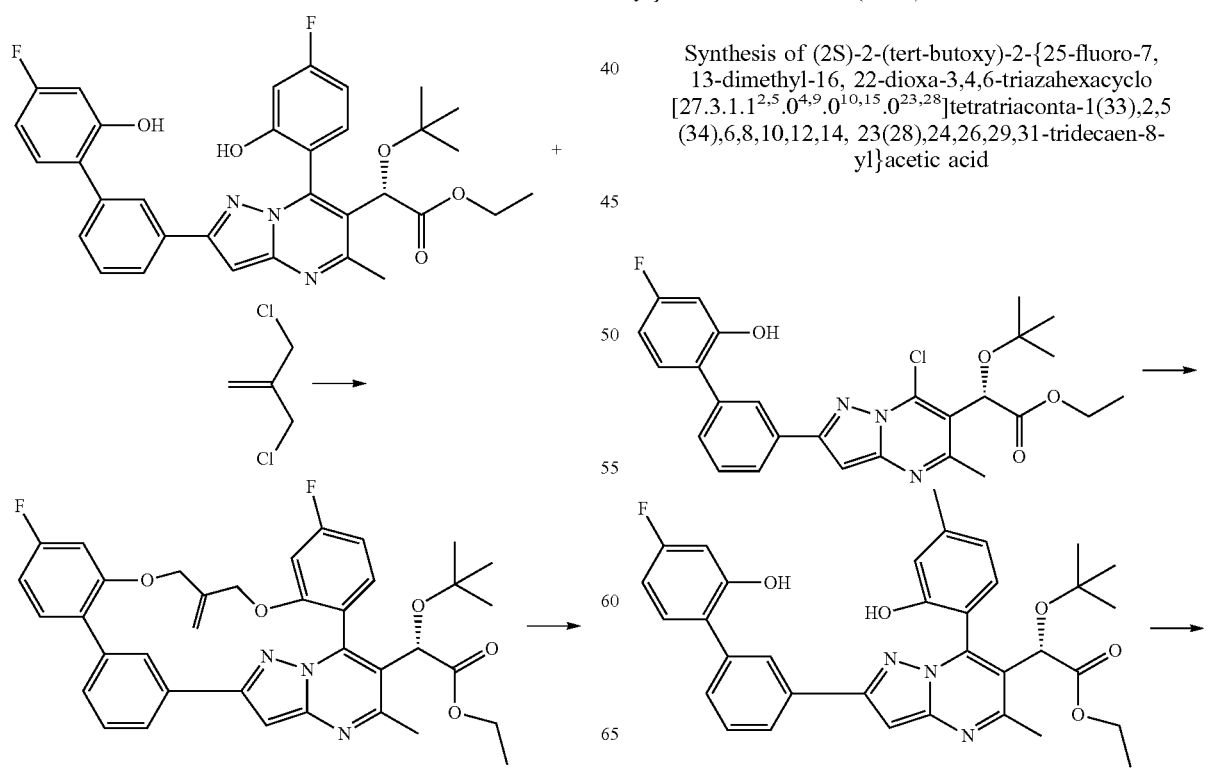

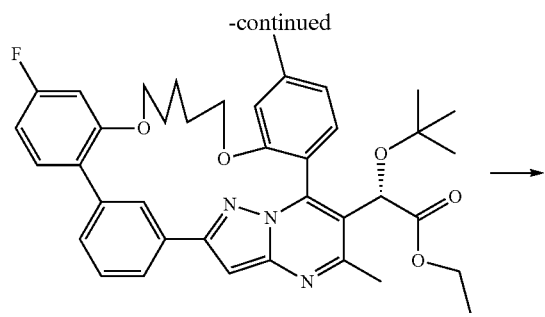
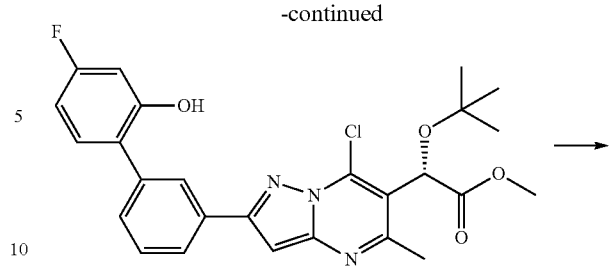

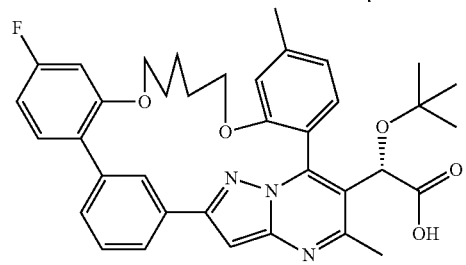

Example 20

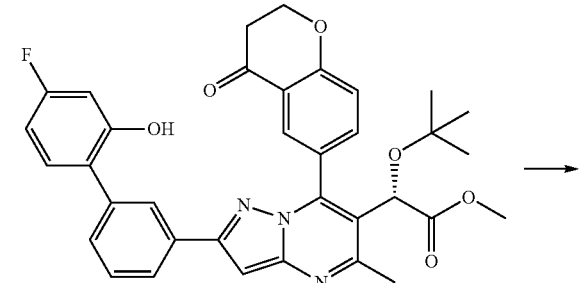

Step 1: K$_2$CO$_3$ (22 mg) and Pd(PPh$_3$)$_4$ (9.03 mg) were added into a solution of(S)-ethyl 2-(tert-butoxy)-2-(7-chloro-2-(4'-fluoro-2'-hydroxy-[1,1'-biphenyl]-3-yl)-5-methylpyrazolo[1,5-a]pyrimidin-6-yl)acetate (40 mg) and (2-hydroxy-4-methylphenyl)boronic acid (14 mg) in dioxane (4 mL) and water (1 mL). The reaction was heated at 90° C. for 16 hours. Concentration of the reaction mixture under vacuum provided a residue which was purified by preparative HPLC. LCMS (M+H)=584.4.

Step 2: Potassium carbonate (6.63 mg) was added into a solution of (2S)-ethyl 2-(tert-butoxy)-2-(2-(4'-fluoro-2'-hydroxy-[1,1'-biphenyl]-3-yl)-7-(2-hydroxy-4-methylphenyl)-5-methylpyrazolo[1,5-a]pyrimidin-6-yl)acetate (14 mg) and 1,5-dibromopentane (5.52 mg) in acetonitrile (3 mL). The reaction was heated at 85° C. for 16 hours. Concentration of the reaction mixture under vacuum provided the crude product which was used as was. LCMS (M+H)=652.3.

Step 3: NaOH (2.76 mg) was added into a solution of ethyl (2S)-2-(tert-butoxy)-2-{25-fluoro-7,13-dimethyl-16, 22-dioxa-3,4,6-triazahexacyclo[27.3.1.1$^{2,5}$.0$^{4,9}$.0$^{10,15}$. 0$^{23,28}$]tetratriaconta-1(33),2,5(34),6,8,10,12,14,23(28),24, 26,29,31-tridecaen-8-yl}acetate (0.015 g, 0.023 mmol) in methanol (1 mL) and water (0.5 mL). The reaction was stirred at room temperature for 16 hours. The reaction mixture was subjected to preparative HPLC to give (2S)-2-(tert-butoxy)-2-{25-fluoro-7,13-dimethyl-16,22-dioxa-3,4, 6-triazahexacyclo[27.3.1.1$^{2,5}$.0$^{4,9}$.0$^{10,15}$.0$^{23,28}$]tetratriaconta-1(33),2,5(34),6,8, 10,12,14,23(28),24,26,29,31-tridecaen-8-yl}) acetic acid (3.2 mg). LCMS (M+H)=624.3.

Synthesis of intermediate (2S)-methyl 2-(tert-butoxy)-2-(2-(4'-fluoro-2'-hydroxy-[1,1'-biphenyl]-3-yl)-7-(4-hydroxychroman-6-yl)-5-methylpyrazolo[1, 5-a]pyrimidin-6-yl)acetate

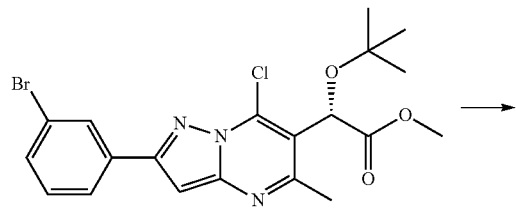

Step 1: A mixture of (S)-methyl 2-(2-(3-bromophenyl)-7-chloro-5-methylpyrazolo[1,5-a]pyrimidin-6-yl)-2-(tert-butoxy)acetate (300 mg, 0.643 mmol), (4-fluoro-2-hydroxyphenyl)boronic acid (110 mg), K$_2$CO$_3$ (178 mg) and [1,1'-bis(diphenylphosphino)ferrocene]dichloropalladium(II) (47.0 mg) in dioxane (8 mL)/water (1.6 mL) was heated at 85° C. in a sealed tube for 4 hours. The mixture was diluted with EtOAc (20 mL), washed with water (20 mL), brine (20 mL), dried over MgSO$_4$ and concentrated under vacuum. The residue was purified by silica gel column (hexanes/ EtOAc=4:1) to give (S)-methyl 2-(tert-butoxy)-2-(7-chloro-2-(4'-fluoro-2'-hydroxy-[1,1'-biphenyl]-3-yl)-5-methylpyrazolo[1,5-a]pyrimidin-6-yl)acetate (200 mg). LCMS (M+H)=498.3.

Step 2: To a mixture of (S)-methyl 2-(tert-butoxy)-2-(7-chloro-2-(4'-fluoro-2'-hydroxy-[1,1'-biphenyl]-3-yl)-5-methylpyrazolo[1,5-a]pyrimidin-6-yl)acetate (200 mg), (4-oxochroman-6-yl)boronic acid (116 mg) and NaHCO$_3$ (101 mg) in dioxane (6 mL)/water (1.5 mL) was added Pd(PPh$_3$)$_4$ (46.4 mg) in a sealed tube. The mixture was heated at 90° C. for 3 hours. The mixture was diluted with EtOAc (20 mL), washed with water (20 mL), brine (20 mL), dried over MgSO$_4$ and concentrated under vacuum. The residue was purified by silica gel column (hexane/EtOAc=2: 1) to give (S)-methyl 2-(tert-butoxy)-2-(2-(4'-fluoro-2'-hydroxy-[1,1'-biphenyl]-3-yl)-5-methyl-7-(4-oxochroman-6-yl)pyrazolo[1,5-a]pyrimidin-6-yl)acetate (180 mg). LCMS (M+H)=610.4.

Step 3: To a solution of(S)-methyl 2-(tert-butoxy)-2-(2-(4'-fluoro-2'-hydroxy-[1,1'-biphenyl]-3-yl)-5-methyl-7-(4-oxochroman-6-yl)pyrazolo[1,5-a]pyrimidin-6-yl)acetate (180 mg) in MeOH (5 mL) was added NaBH$_4$ (22.34 mg) at 0° C. After stirring 2 hours at 0° C., the reaction was quenched with water. The mixture was diluted wit EtOAc (20 mL), washed with brine (20 mL), dried over MgSO$_4$ and concentrated under vacuum to give (2S)-methyl 2-(tert-butoxy)-2-(2-(4'-fluoro-2'-hydroxy-[1,1'-biphenyl]-3-yl)-7-(4-hydroxychroman-6-yl)-5-methylpyrazolo[1,5-a]pyrimidin-6-yl)acetate (120 mg). LCMS (M+H)=612.3.

Synthesis of (2S)-2-(tert-Butoxy)-2-{18-fluoro-4-methyl-21,27,31-trioxa-5,7,8-triazaheptacyclo[26.6.2.1$^{6,9}$.1$^{10,14}$.0$^{2,7}$.0$^{15,20}$.0$^{32,36}$]octatriaconta-1(34),2,4,6(38),8,10(37),11,13,15(20),16,18,32,35-tridecaen-3-yl}acetic acid

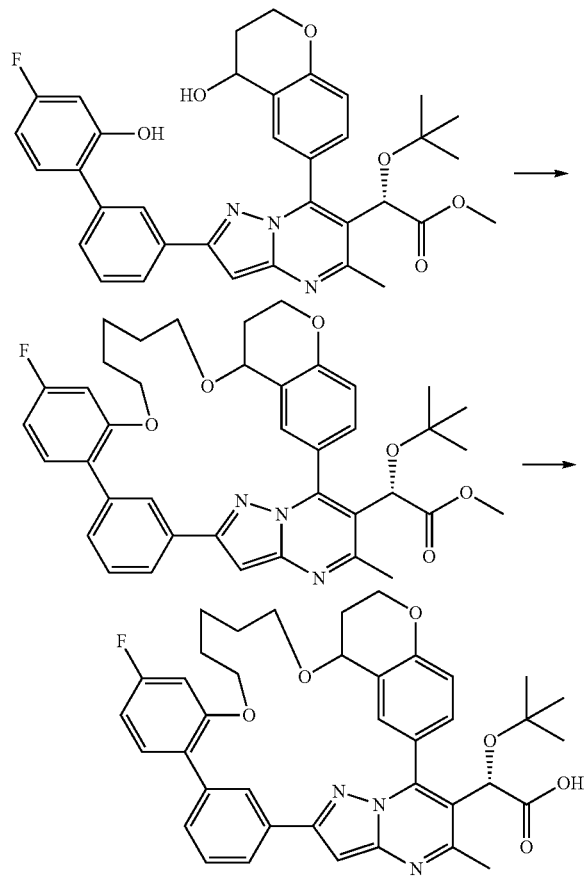

Example 21

Step 1: To a solution of (2S)-methyl 2-(tert-butoxy)-2-(2-(4'-fluoro-2'-hydroxy-[1,1'-biphenyl]-3-yl)-7-(4-hydroxychroman-6-yl)-5-methylpyrazolo[1,5-a]pyrimidin-6-yl)acetate (10 mg) and Cs$_2$CO$_3$ (32.0 mg) in DMF (5 mL) was added 1,5-diiodopentane (5.30 mg) in 1 mL of DMF dropwise. The mixture was stirred at room temperature for 6 hours. The solvent was removed under vacuum. The residue was purified by preparative HPLC to give methyl (2S)-2-(tert-butoxy)-2-{18-fluoro-4-methyl-21,27,31-trioxa-5,7,8-triazaheptacyclo[26.6.2.1$^{6,9}$.1$^{10,14}$.0$^{2,7}$.0$^{15,20}$.0$^{32,36}$]octatriaconta-1(34),2,4,6(38),8,10(37),11,13,15(20),16,18,32,35-tridecaen-3-yl}acetate (3 mg). LCMS (M+H)=680.1.

Step 2: To a solution of methyl (2S)-2-(tert-butoxy)-2-{18-fluoro-4-methyl-21,27,31-trioxa-5,7,8-triazaheptacyclo[26.6.2.1$^{6,9}$.1$^{10,14}$.0$^{2,7}$.0$^{15,20}$.0$^{32,36}$]octatriaconta-1(34),2,4,6(38),8,10(37),11,13,15(20),16,18,32,35-tridecaen-3-yl}acetate (3 mg) in MeOH (0.5 mL)/THF (0.25 mL)/water (0.5 mL) was added NaOH (0.088 mL, 1N). The mixture was stirred at room temperature for 4 hours. The mixture was acidified by 1N HCl to pH ~4. All the solvents were removed under vacuum. The residue was purified by preparative HPLC to give (2S)-2-(tert-butoxy)-2-{18-fluoro-4-methyl-21,27,31-trioxa-5,7,8-triazaheptacyclo[26.6.2.1$^{6,9}$.1$^{10,14}$.0$^{2,7}$.0$^{15,20}$.0$^{32,36}$]octatriaconta-1(34),2,4,6(38),8,10(37),11,13,15(20),16,18,32,35-tridecaen-3-yl}acetic acid (1.1 mg). LCMS (M+H)=666.2.

Synthesis of (2S)-2-(tert-butoxy)-2-{18-fluoro-4-methyl-21,28,32-trioxa-5,7,8-triazaheptacyclo[27.6.2.1$^{6,9}$.1$^{10,14}$.0$^{2,7}$.0$^{15,20}$.0$^{33,37}$]nonatriaconta-1(35),2,4,6(39),8,10(38),11,13,15(20),16,18,33,36-tridecaen-3-yl}acetic acid

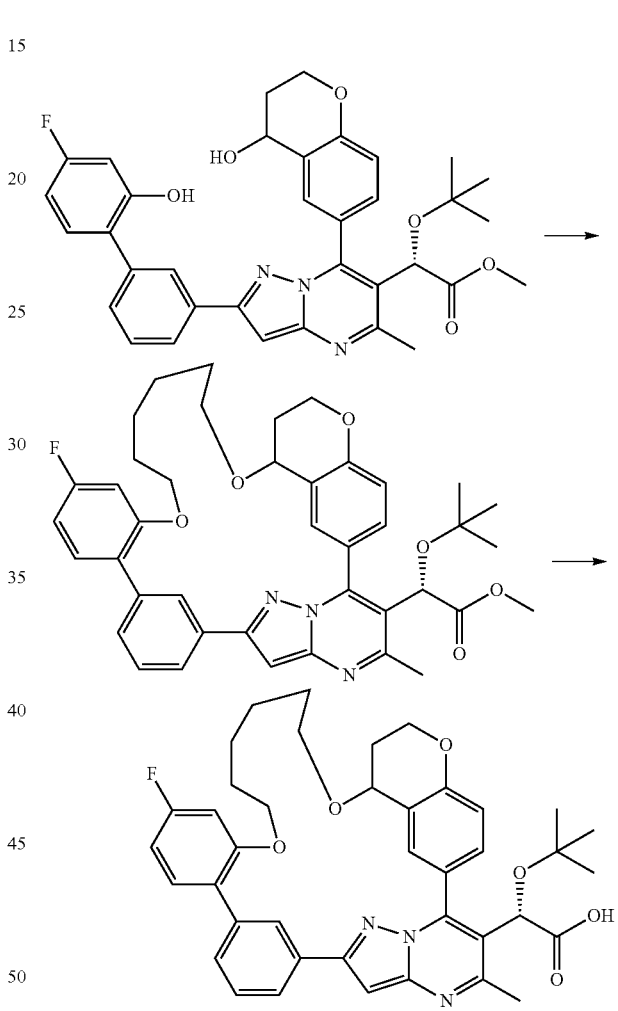

Example 22

Step 1: To a solution of (2S)-methyl 2-(tert-butoxy)-2-(2-(4'-fluoro-2'-hydroxy-[1,1'-biphenyl]-3-yl)-7-(4-hydroxychroman-6-yl)-5-methylpyrazolo[1,5-a]pyrimidin-6-yl)acetate (15 mg) and 1,6-diiodohexane (12.43 mg) in DMF (7 mL) was added Cs$_2$CO$_3$ (32.0 mg). The mixture was stirred at room temperature for 16 hours. The solvent was removed under vacuum. The residue was purified by preparative HPLC to give methyl (2S)-2-(tert-butoxy)-2-{18-fluoro-4-methyl-21,28,32-trioxa-5,7,8-triazaheptacyclo[27.6.2.1$^{6,9}$.1$^{10,14}$.0$^{2,7}$.0$^{15,20}$.0$^{33,37}$]nonatriaconta-1(35),2,4,6(39),8,10(38),11,13,15(20),16,18,33,36-tridecaen-3-yl}acetate (4 mg). LCMS (M+H)=694.2.

Step 2: To a solution of a mixture methyl (2S)-2-(tert-butoxy)-2-{18-fluoro-4-methyl-21,28,32-trioxa-5,7,8-triazaheptacyclo[27.6.2.1$^{6,9}$.1$^{10,14}$.0$^{2,7}$.0$^{15,20}$.0$^{33,37}$]nonatria-conta-1(35),2,4,6(39),8,10(38),11,13,15(20),16,18,33,36-tridecaen-3-yl}acetate (4 mg) in MeOH (0.5 mL)/THF (0.25 mL)/water (0.5 mL) was added NaOH (0.115 mL, 1N). The mixture was stirred at room temperature for 4 hours. The mixture was acidified by 1N HCl to pH ~4. All the solvents were removed under vacuum. The residue was purified by preparative HPLC to give (2S)-2-(tert-butoxy)-2-{18-fluoro-4-methyl-21,28,32-trioxa-5,7,8-triazaheptacyclo [27.6.2.1$^{6,9}$.1$^{10,14}$.0$^{2,7}$.0$^{15,20}$.0$^{33,37}$]nonatriaconta-1(35),2,4,6(39),8,10(38),11,13,15(20),16,18,33,36-tridecaen-3-yl}acetic acid (0.9 mg). LCMS (M+H)=680.1.

Synthesis of (2S)-2-(tert-butoxy)-2-{18-fluoro-4-methyl-21, 29, 33-trioxa-5, 7, 8-triazaoctacyclo [28.6.2.1$^{6,9}$.1$^{10,14}$.1$^{23,27}$.0$^{2,7}$.0$^{15,20}$.0$^{34,38}$]hentetraconta-1(36),2,4,6(41),8,10(40),11,13,15(20),16,18, 23, 25, 27(39),34,37-hexadecaen-3-yl}acetic acid residue which was purified by prep HPLC to give (2S)-methyl 2-(2-(2'-((3-(bromomethyl)benzyl)oxy)-4'-fluoro-[1,1'-biphenyl]-3-yl)-7-(4-hydroxychroman-6-yl)-5-methylpyrazolo[1,5-a]pyrimidin-6-yl)-2-(tert-butoxy)acetate (16 mg). LCMS (M+H)=794.3.

Step 2: To a solution of (2S)-methyl 2-(2-(2'-((3-(bromomethyl)benzyl)oxy)-4'-fluoro-[1,1'-biphenyl]-3-yl)-7-(4-hydroxychroman-6-yl)-5-methylpyrazolo[1,5-a]pyrimidin-6-yl)-2-(tert-butoxy)acetate (11 mg) in THF (5 mL) was added NaH (2.77 mg, 60%). The reaction was stirred at room temperature for 5 hours before being quenched with water (2 mL). The mixture was stirred at room temperature for 2 hours, before it was acidified by 1N HCl to pH=3. All the solvents were removed under vacuum to give a residue which was purified by preparative HPLC to give (2S)-2-(tert-butoxy)-2-{18-fluoro-4-methyl-21,29,33-trioxa-5,7,8-triazaoctacyclo[28.6.2.1$^{6,9}$.1$^{10,14}$.1$^{23,27}$.0$^{2,7}$.0$^{15,20}$.0$^{34,38}$] hentetraconta 1(36),2,4,6(41),8,10(40),11,13,15(20),16,18,23,25,27(39),34,37-hexadecaen-3-yl}acetic acid (0.7 mg). LCMS (M+H)=700.2.

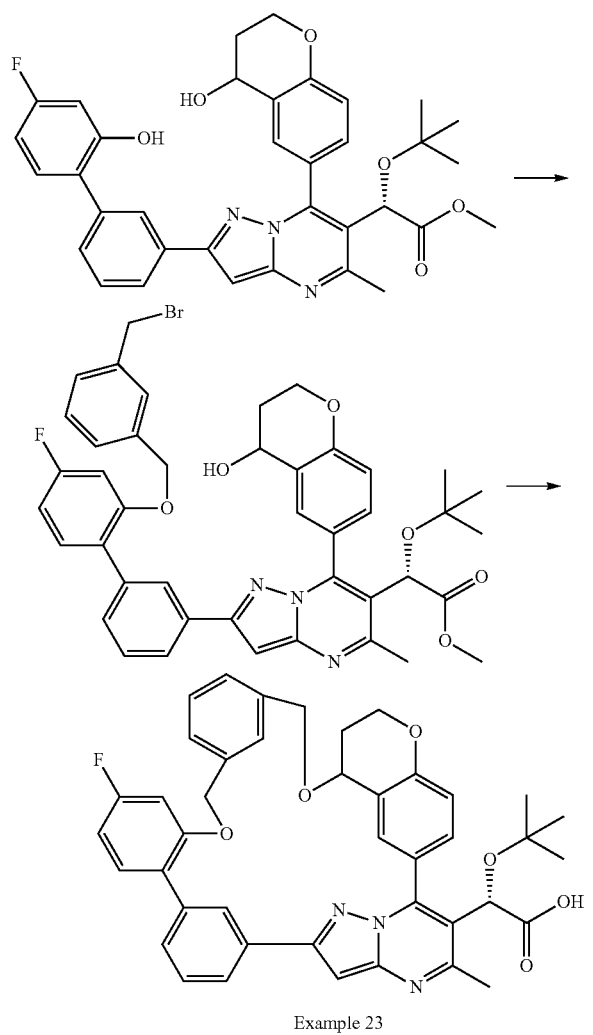

Example 23

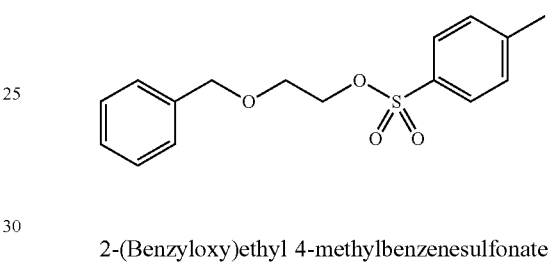

2-(Benzyloxy)ethyl 4-methylbenzenesulfonate

To a solution of 2-(benzyloxy)ethanol (1.47 g, 9.66 mmol, 1 equiv) and TEA (2.83 mL, 20.28 mmol, 2.1 equiv) was added TsCl (2.2 g, 11.59 mmol, 1.2 equiv). After stirring 18 h, the reaction was added to saturated aqueous NaHCO$_3$ and extracted with DCM (×2). The combined DCM extracts were dried (Na$_2$SO$_4$) and concentrated in vacuo. The crude product was purified by flash column chromatography (0-50% EtOAc in hexane) to provide the product as a viscous colorless oil (2.75 g, 93%). $^1$H NMR (500 MHz, CDCl$_3$) δ 7.89-7.78 (m, 2H), 7.41-7.23 (m, 7H), 4.51 (s, 2H), 4.27-4.20 (m, 2H), 3.76-3.62 (m, 2H), 2.46 (s, 3H).

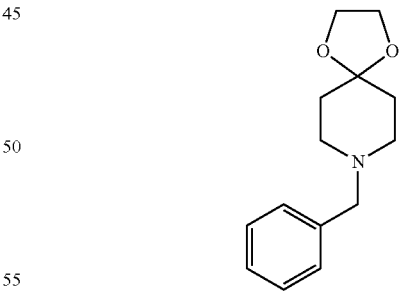

8-Benzyl-1, 4-dioxa-8-azaspiro[4.5]decane

Step 1: To a solution of (2S)-methyl 2-(tert-butoxy)-2-(2-(4'-fluoro-2'-hydroxy-[1,1'-biphenyl]-3-yl)-7-(4-hydroxychroman-6-yl)-5-methylpyrazolo[1,5-a]pyrimidin-6-yl)acetate (20 mg) and 1,3-bis(bromomethyl)benzene (17.26 mg) in DMF (3 mL) was added cesium carbonate (42.6 mg). The reaction mixture was stirred at room temperature for 4 hours. All the solvents were removed under vacuum to give a To a solution of 1,4-dioxa-8-azaspiro[4.5]decane (5.1 g, 35.6 mmol, 1 equiv) in DMF (71 mL) was added K$_2$CO$_3$ (9.6 g, 71.2 mmol, 2 equiv) and BnBr (5.1 mL, 42.7 mmol, 1.2 equiv). After 1 h, the reaction was diluted with ether and washed with water and brine. The ether layer was dried (MgSO$_4$) and concentrated in vacuo. The crude product was purified by flash column chromatography (0-100% EtOAc [2% TEA] in hexane) to provide the product as a viscous pale tan oil (6.8 g, 82%). $^1$H NMR (400 MHz, CDCl$_3$) δ 7.35-7.28 (m, 5H), 3.96 (s, 4H), 3.54 (s, 2H), 2.54 (br. s., 4H), 1.76 (t, J=5.6 Hz, 4H).

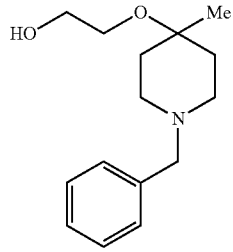 [SMILES: CC1(OCCO)CCN(Cc2ccccc2)CC1]

2-((1-Benzyl-4-methylpiperidin-4-yl)oxy)ethanol

To a solution of 8-benzyl-1,4-dioxa-8-azaspiro[4.5]decane (1 g, 4.29 mmol, 1 equiv) was added MeMgBr (4.29 mL of a 3 M solution in ether, 12.86 mmol, 3 equiv). The reaction was slowly heated to 90° C. allowing the ether portion to boil off. After heating for 18 h, the gray slurry was allowed to cool to ambient temperature. The reaction was added cautiously to saturated aqueous NH$_4$Cl and extracted with DCM (×3). The combined DCM extracts were dried (Na$_2$SO$_4$) and concentrated in vacuo. The crude product was purified by flash column chromatography (0-100% EtOAc [2% TEA] in hexane) to provide the product as a colorless oil (0.73 g, 68%). $^1$H NMR (500 MHz, CDCl$_3$) δ 7.36-7.27 (m, 5H), 3.73 (br. s., 2H), 3.52 (s, 2H), 3.49-3.42 (m, 2H), 2.58-2.49 (m, 2H), 2.41-2.32 (m, 2H), 2.12-2.08 (m, 1H), 1.83-1.76 (m, 2H), 1.65-1.56 (m, 2H), 1.19 (s, 3H); LCMS (ESI, M+1): 250.15.

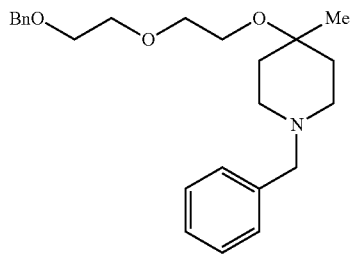 [SMILES: CC1(OCCOCCOCc2ccccc2)CCN(Cc2ccccc2)CC1]

1-Benzyl-4-(2-(2-(benzyloxy)ethoxy)ethoxy)-4-methylpiperidine

To a solution of 2-((1-benzyl-4-methylpiperidin-4-yl)oxy)ethanol (0.28 g, 1.123 mmol, 1 equiv) in DMF (5.6 mL) was added 60% NaH (63 mg, 1.572 mmol, 1.4 equiv). After 5 min, 2-(benzyloxy)ethyl 4-methylbenzenesulfonate (0.55 g, 1.797 mmol, 1.6 equiv). After stirring 2 h, the reaction was partitioned between 1 N NaOH and EtOAc. EtOAc layer washed with brine, dried (Na$_2$SO$_4$), and concentrated in vacuo. The crude product was purified by flash column chromatography (0-100% EtOAc[2% TEA] in hexane) to provide the product as a viscous pale tan oil (0.31 g, 72%). $^1$H NMR (500 MHz, CDCl$_3$) δ 7.42-7.29 (m, 10H), 4.62 (s, 2H), 3.75-3.71 (m, 2H), 3.68-3.64 (m, 4H), 3.53-3.49 (m, 4H), 2.55-2.45 (m, 2H), 2.38 (br. s., 2H), 1.82-1.74 (m, 2H), 1.59-1.53 (m, 2H), 1.17 (s, 3H); LCMS (ESI, M+1): 384.7.

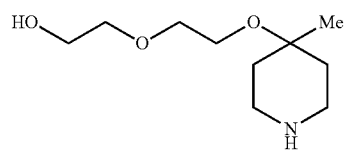 [SMILES: CC1(OCCOCCO)CCNCC1]

2-(2-((4-Methylpiperidin-4-yl)oxy)ethoxy)ethanol

To a solution of 1-benzyl-4-(2-(2-(benzyloxy)ethoxy)ethoxy)-4-methylpiperidine (0.31 g, 0.808 mmol, 1 equiv) and 1 M HCl (0.97 mL, 0.97 mmol, 1.2 equiv) in MeOH (8 mL) was added 10% Pd/C (0.086 g, 0.081 mmol, 0.1 equiv). The reaction was put under a balloon of H$_2$ and stirred 2 d. The reaction was filtered through Celite eluting with MeOH. The filtrate was then concentrated in vacuo to provide the HCl salted product as a gummy solid (0.21 g, ~100%). $^1$H NMR (500 MHz, CD$_3$OD) δ 3.72-3.68 (m, 2H), 3.67-3.64 (m, 2H), 3.62-3.59 (m, 2H), 3.57-3.54 (m, 2H), 3.35-3.29 (m, 2H), 3.20-3.14 (m, 2H), 2.07-2.01 (m, 2H), 1.75-1.66 (m, 2H), 1.28 (s, 3H); LCMS (ESI, M+1): 204.2.

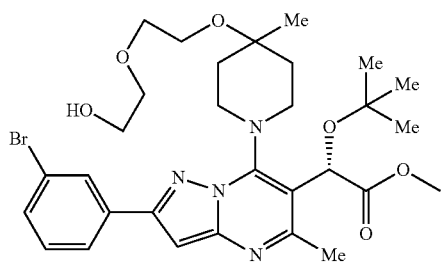 [SMILES: COC(=O)[C@@H](OC(C)(C)C)c1c(C)nc2cc(-c3cccc(Br)c3)nn2c1N1CCC(C)(OCCOCCO)CC1]

(S)-Methyl 2-(2-(3-bromophenyl)-7-(4-(2-(2-hydroxyethoxy)ethoxy)-4-methylpiperidin-1-yl)-5-methylpyrazolo[1,5-a]pyrimidin-6-yl)-2-(tert-butoxy)acetate A solution of (S)-methyl 2-(2-(3-bromophenyl)-7-chloro-5-methylpyrazolo[1,5-a]pyrimidin-6-yl)-2-(tert-butoxy)acetate (0.27 g, 0.578 mmol, 1 equiv) and 2-(2-((4-methylpiperidin-4-yl)oxy)ethoxy)ethanol hydrochloride (0.208 g, 0.868 mmol, 1.5 equiv), and DIPEA (0.303 mL, 1.735 mmol, 3 equiv) in DMF (2.9 mL) was heated at 60° C. for 5 h. The temperature was then raised to 80° C. for 2 h. Upon cooling to ambient temperature, the reaction was added to saturated aqueous NaHCO$_3$ and extracted with DCM (×3). The combined DCM extracts were dried (Na$_2$SO$_4$) and concentrated in vacuo. The crude product was purified by flash column chromatography (0-100% EtOAc in hexane) to provide the product as a off white foam (0.29 g, 79%). $^1$H NMR (500 MHz, CDCl$_3$) [note: 4H of piperidine not observed, likely very broad] δ 8.23-8.14 (m, 1H), 7.96-7.88 (m, 1H), 7.56-7.50 (m, 1H), 7.35 (s, 1H), 6.81 (s, 1H), 6.06-5.85 (m, 1H), 3.90-3.83 (m, 2H), 3.76 (s, 3H), 3.73 (s, 4H), 3.69-3.63 (m, 2H), 2.70-2.65 (m, 1H), 2.63 (s, 3H), 2.06-1.94 (m, 3H), 1.83-1.68 (m, 1H), 1.43-1.35 (m, 3H), 1.27 (s, 9H); LCMS (ESI, M+1): 635.4.

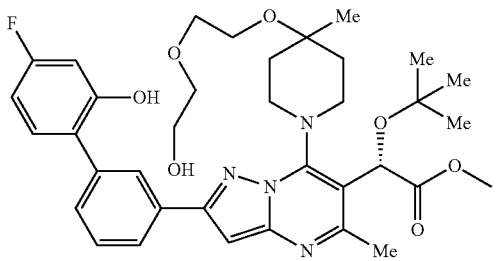 [SMILES: COC(=O)[C@@H](OC(C)(C)C)c1c(C)nc2cc(-c3cccc(-c4ccc(F)cc4O)c3)nn2c1N1CCC(C)(OCCOCCO)CC1]

(S)-Methyl 2-(tert-butoxy)-2-(2-(4'-fluoro-2'-hydroxy-[1,1'-biphenyl]-3-yl)-7-(4-(2-(2-hydroxyethoxy)ethoxy)-4-methylpiperidin-1-yl)-5-methylpyrazolo[1,5-a]pyrimidin-6-yl)acetate To a solution of (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (0.090 g, 0.142 mmol, 1 equiv), (4-fluoro-2-hydroxyphenyl)boronic acid (44 mg, 0.284 mmol, 2 equiv), and Pd(PPh₃)₄ (16 mg, 0.014 mmol, 0.1 equiv) was added Na₂CO₃ (0.14 mL of a 2 M aqueous solution, 0.284 mmol, 2 equiv). The reaction was heated to 90° C. for 3 h. Upon cooling to ambient temperature, the reaction was added to water and extracted with DCM (×4). The combined DCM extracts were dried (Na₂SO₄) and concentrated in vacuo. The crude product was purified by flash column chromatography (0-100% EtOAc in hexane) to provide the product as a yellow foam (0.080 g, 85%). ¹H NMR (400 MHz, CDCl₃) δ 8.31 (br. s., 1H), 7.91 (d, J=5.8 Hz, 1H), 7.61-7.50 (m, 2H), 7.45 (d, J=7.8 Hz, 1H), 7.35-7.29 (m, 1H), 6.83 (s, 1H), 6.77-6.69 (m, 2H), 5.90 (br. s., 1H), 4.58-4.29 (m, 1H), 3.85-3.55 (m, 14H), 3.21 (br. s., 2H), 2.01-1.88 (m, 1H), 1.71 (d, J=10.8 Hz, 2H), 1.35 (br. s., 3H), 1.25 (s, 9H); ¹⁹F NMR (376 MHz, CDCl₃) δ−113.22 (br. s., 1F); LCMS (ESI, M+1): 665.5.

Example 24

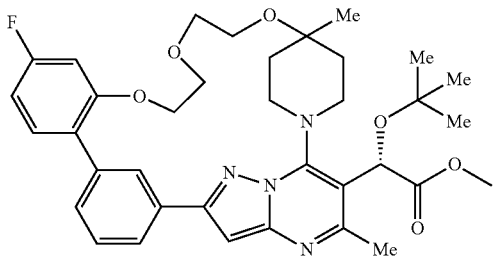 [SMILES: COC(=O)[C@@H](OC(C)(C)C)c1c(C)nc2cc3nn2c1N1CCC(C)(CC1)OCCOCCOc1cc(F)ccc1-c1cccc-3c1]

(2S)-2-(tert-Butoxy)-2-{18-fluoro-4,28-dimethyl-21,24,27-trioxa-1,5,7,8-tetraazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl}acetic acid To a solution of (S)-methyl 2-(tert-butoxy)-2-(2-(4'-fluoro-2'-hydroxy-[1,1'-biphenyl]-3-yl)-7-(4-(2-(2-hydroxyethoxy)ethoxy)-4-methylpiperidin-1-yl)-5-methylpyrazolo[1,5-a]pyrimidin-6-yl)acetate (0.080 g, 0.120 mmol, 1 equiv) and PPh₃ (0.047 g, 0.181 mmol, 1.5 equiv) in THF (24 mL) was added DIAD (0.035 mL, 0.181 mmol, 1.5 equiv). After stirring 1 h, a few drops of water were added to the reaction and the mixture was concentrated in vacuo. The crude product was purified by flash column chromatography (0-100% EtOAc in hexane) to provide the product as a white solid (0.102 g) partially contaminated with a byproduct. ¹H NMR (500 MHz, DMSO-d₆) δ 8.42 (s, 1H), 7.88 (d, J=7.7 Hz, 1H), 7.53 (t, J=7.7 Hz, 1H), 7.37-7.31 (m, 2H), 7.19-7.12 (m, 1H), 7.03 (s, 1H), 6.90-6.83 (m, 1H), 5.65 (s, 1H), 4.53-4.38 (m, 2H), 4.16-4.03 (m, 2H), 3.92-3.81 (m, 1H), 3.69 (br. s., 1H), 3.61 (d, J=8.8 Hz, 2H), 3.56-3.39 (m, 2H), 3.36-3.27 (m, 1H), 2.80 (d, J=11.4 Hz, 1H), 2.53 (s, 3H), 1.96-1.87 (m, 2H), 1.76-1.67 (m, 1H), 1.58 (d, J=3.7 Hz, 1H), 1.19 (s, 3H), 1.16 (s, 9H); LCMS (ESI, M+1): 633.7. To a solution of impure methyl (2S)-2-(tert-butoxy)-2-{18-fluoro-4,28-dimethyl-21,24,27-trioxa-1,5,7,8-tetraazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl}acetate in 10:1 MeOH:water (2 mL) was added LiOH—H₂O (199 mg, 473 mmol, 30 equiv). The reaction was heated to 70° C. for 1.5 h. Upon cooling to ambient temperature, the reaction was filtered and purified via preparative LC/MS with the following conditions: Column: XBridge C18, 19×mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-80% B over 15 minutes, then a 5-minute hold at 100% B; Flow: 20 mL/min to provide the product (54 mg, 72% for 2 steps). 1H NMR (500 MHz, DMSO-d₆) δ 8.42 (s, 1H), 7.88 (d, J=7.7 Hz, 1H), 7.53 (t, J=7.7 Hz, 1H), 7.37-7.31 (m, 2H), 7.19-7.12 (m, 1H), 7.03 (s, 1H), 6.90-6.83 (m, 1H), 5.65 (s, 1H), 4.53-4.38 (m, 2H), 4.16-4.03 (m, 2H), 3.92-3.81 (m, 1H), 3.69 (br. s., 1H), 3.61 (d, J=8.8 Hz, 2H), 3.56-3.39 (m, 2H), 3.36-3.27 (m, 1H), 2.80 (d, J=11.4 Hz, 1H), 2.53 (s, 3H), 1.96-1.87 (m, 2H), 1.76-1.67 (m, 1H), 1.58 (d, J=3.7 Hz, 1H), 1.19 (s, 3H), 1.16 (s, 9H); LCMS (ESI, M+1): 633.7.

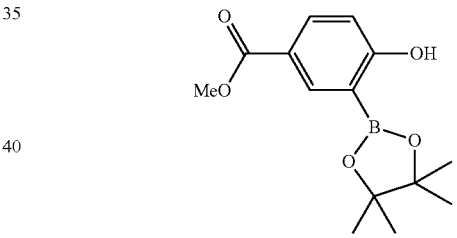

Methyl 4-hydroxy-3-(4, 4, 5, 5-tetramethyl-1, 3, 2-dioxaborolan-2-yl)benzoate

A mixture of methyl 3-bromo-4-hydroxybenzoate (3 g, 12.98 mmol), bis(pinocolato)diboron (6.59 g, 26.0 mmol), 1,1'-bis(diphenylphosphine)ferrocene (0.360 g, 0.649 mmol) and KOAc (3.82 g, 39.0 mmol) in 1,4-dioxane (70 mL) was sparged with N₂ for 15 min. Then, 1,1-bis(diphenylphosphino)ferrocene]dichloropalladium(II) CH₂Cl₂ complex (0.530 g, 0.649 mmol) was added, sparged for additional 5 min and heated at 85° C. for 16 h. Then, cooled, diluted with Et₂O (250 mL), washed with water (4×50 mL), brine (25 mL), dried (Na₂SO₄), filtered and concentrated to give brow paste which was purified by flash chromatography (5-25% EtOAc/hexane) to afford methyl 4-hydroxy-3-(4,4,5,5-tetramethyl-1,3,2-dioxaborolan-2-yl)benzoate (1.2 g, 4.31 mmol, 33.2% yield) as white solid. ¹H NMR (500 MHz, CDCl₃) δ 8.36 (d, J=2.4 Hz, 1H), 8.30-8.21 (m, 1H), 8.13-8.02 (m, 1H), 6.93 (d, J=8.7 Hz, 1H), 3.90 (s, 3H), 1.41 (s, 12H).

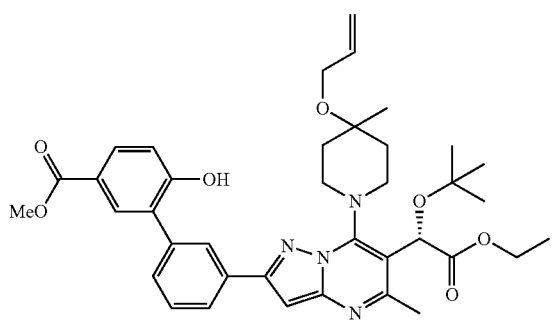 [SMILES: C=CCOC1(C)CCN(c2c([C@H](OC(C)(C)C)C(=O)OCC)c(C)nc3cc(-c4cccc(-c5cc(C(=O)OC)ccc5O)c4)nn23)CC1]

(S)-Methyl 3'-(7-(4-(allyloxy)-4-methylpiperidin-1-yl)-6-(1-(tert-butoxy)-2-ethoxy-2-oxoethyl)-5-methylpyrazolo[1,5-a]pyrimidin-2-yl)-6-hydroxy-[1,1'-biphenyl]-3-carboxylate A solution of ((S)-ethyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (500 mg, 0.834 mmol), methyl 4-hydroxy-3-(4,4,5,5-tetramethyl-1,3,2-dioxaborolan-2-yl)benzoate (348 mg, 1.251 mmol) and 2.0 M $Na_2CO_3$ (1.042 mL, 2.085 mmol) in DMF (10 mL) was degassed for 10 min. $Pd(Ph_3P)_4$ (67.5 mg, 0.058 mmol), was added and the degassing was continued for another 5 min. The reaction was then heated at 90° C. for 3 hrs. At this point LCMS indicated completion of reaction. The mixture was then cooled to room temp and diluted with water (25 mL) and extracted with $Et_2O$ (2×50 mL). The combined extracts were dried ($Na_2SO_4$), filtered, and concentrated under reduced pressure, and the residue was purified by BIOTAGE™ flash chromatography purification system (0-25% EtOAc/hexane) to afford (S)-methyl 3'-(7-(4-(allyloxy)-4-methylpiperidin-1-yl)-6-(1-(tert-butoxy)-2-ethoxy-2-oxoethyl)-5-methylpyrazolo[1,5-a]pyrimidin-2-yl)-6-hydroxy-[1,1'-biphenyl]-3-carboxylate (480 mg, 0.716 mmol, 86% yield) as white foam. $^1$H NMR (500 MHz, $CDCl_3$) δ 8.16-8.12 (m, 1H), 8.09-8.04 (m, 2H), 8.03-7.98 (m, 1H), 7.61-7.56 (m, 1H), 7.52-7.45 (m, 1H), 7.09 (d, J=8.5 Hz, 1H), 6.88 (br. s., 1H), 6.07-5.85 (m, 2H), 5.45-5.34 (m, 1H), 5.11 (br. s., 1H), 4.32-4.18 (m, 2H), 4.01 (d, J=4.9 Hz, 2H), 3.92 (s, 3H), 2.64 (s, 3H), 2.05-1.95 (m, 2H), 1.74 (br. s., 1H), 1.63 (br. s., 3H), 1.39-1.32 (m, 3H), 1.28-1.25 (m, 15H). LCMS (M+H)=671.6.

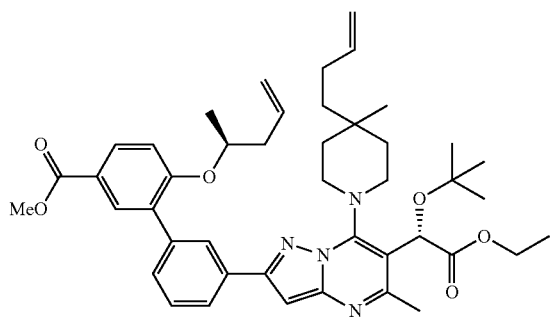 [SMILES: C=CCCC1(C)CCN(c2c([C@H](OC(C)(C)C)C(=O)OCC)c(C)nc3cc(-c4cccc(-c5cc(C(=O)OC)ccc5O[C@@H](C)CC=C)c4)nn23)CC1]

Methyl 3'-(7-(4-(but-3-en-1-yl)-4-methylpiperidin-1-yl)-6-((S)-1-(tert-butoxy)-2-ethoxy-2-oxoethyl)-5-methylpyrazolo[1,5-a]pyrimidin-2-yl)-6-((S)-pent-4-en-2-yloxy)-[1,1'-biphenyl]-3-carboxylate To a solution of (S)-methyl 3'-(7-(4-(but-3-en-1-yl)-4-methylpiperidin-1-yl)-6-(1-(tert-butoxy)-2-ethoxy-2-oxoethyl)-5-methylpyrazolo[1,5-a]pyrimidin-2-yl)-6-hydroxy-[1,1'-biphenyl]-3-carboxylate (480 mg, 0.718 mmol) and (R)-pent-4-en-2-ol (185 mg, 2.153 mmol) in THF (8 mL) was added $Ph_3P$ (565 mg, 2.153 mmol) follows by DEAD (0.341 mL, 2.153 mmol) and the resulting mixture was stirred at room temp for 3 h. Water (10 mL) was then added and the mixture was extracted with ether (50 mL), washed with brine (10 mL), dried ($Na_2SO_4$), filtered and concentrated. The residue was then purified via BIOTAGE™ flash chromatography purification system (0-20% EtOAc/hexane) to afford methyl 3'-(7-(4-(but-3-en-1-yl)-4-methylpiperidin-1-yl)-6-((S)-1-(tert-butoxy)-2-ethoxy-2-oxoethyl)-5-methylpyrazolo[1,5-a]pyrimidin-2-yl)-6-((S)-pent-4-en-2-yloxy)-[1,1'-biphenyl]-3-carboxylate (450 mg, 0.611 mmol, 85% yield) as white solid. $^1$H NMR (500 MHz, $CDCl_3$) δ 8.16-8.10 (m, 2H), 8.09-8.00 (m, 2H), 7.56 (br. s., 1H), 7.51 (t, J=7.6 Hz, 1H), 7.04 (d, J=8.7 Hz, 1H), 6.87 (br. s., 1H), 6.05-5.95 (m, 1H), 5.85-5.73 (m, 2H), 5.41 (dd, J=17.1, 1.5 Hz, 1H), 5.17-5.02 (m, 4H), 4.59 (sxt, J=6.1 Hz, 1H), 4.29-4.17 (m, 4H), 4.02 (d, J=4.6 Hz, 2H), 3.93 (s, 3H), 2.67 (br. s., 2H), 2.53-2.43 (m, 1H), 2.40-2.30 (m, 2H), 2.20 (br. s., 1H), 2.04 (d, J=15.4 Hz, 2H), 1.75 (br. s., 1H), 1.35-1.32 (m, 3H), 1.32-1.24 (m, 15H), 1.21-1.15 (m, 3H). LCMS (M+H)=737.6.

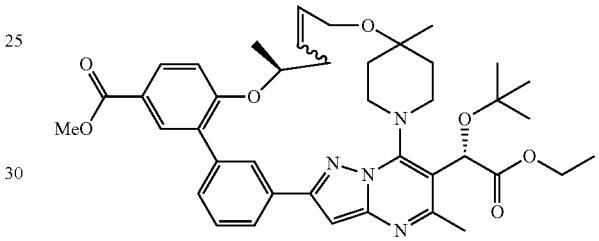

Methyl (22S)-3-[(1S)-1-(tert-butoxy)-2-ethoxy-2-oxoethyl]-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaene-17-carboxylate To a solution of methyl 3'-(7-(4-(allyloxy)-4-methylpiperidin-1-yl)-6-((S)-1-(tert-butoxy)-2-ethoxy-2-oxoethyl)-5-methylpyrazolo[1,5-a]pyrimidin-2-yl)-6-((S)-pent-4-en-2-yloxy)-[1,1'-biphenyl]-3-carboxylate (450 mg, 0.609 mmol) in DCE (400 mL) at room temp was added CuI (116 mg, 0.609 mmol) followed by (1,3-dimesitylimidazolidin-2-ylidene)(2-isopropoxybenzylidene)ruthenium(VI) chloride (38.2 mg, 0.061 mmol) and the resulting mixture was heated at 80° C. for 3 h. At this point LCMS indicated completion of reaction. Mixture was then cooled to room temp, filtered and concentrated to afford brown solid which was purified by BIOTAGE™ flash chromatography purification system (5-30% etOAc/hexane) to afford methyl (22S)-3-[(1S)-1-(tert-butoxy)-2-ethoxy-2-oxoethyl]-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaene-17-carboxylate (360 mg, 0.506 mmol, 83% yield) as approx 1:4 mixture of cis and trans isomer. Major isomer was transcribed $^1$H NMR (400 MHz, $CDCl_3$) δ 8.52-8.48 (m, 1H), 8.07-8.00 (m, 2H), 7.85 (d, J=8.0 Hz, 1H), 7.56-7.49 (m, 1H), 7.38-7.29 (m, 1H), 7.04-6.99 (m, 1H), 6.95 (br. s., 1H), 6.44-6.30 (m, 1H), 5.94 (br. s., 1H), 5.68 (d, J=15.6 Hz, 1H), 4.89 (t, J=11.5 Hz, 1H), 4.63 (t, J=6.5 Hz, 1H), 4.29-4.17 (m, 3H), 3.99 (br. s., 2H), 3.92-3.90 (m, 3H), 3.75 (t, J=11.4 Hz, 1H), 3.23 (d, J=10.3 Hz, 1H), 2.89 (d, J=13.3 Hz, 1H), 2.64 (s, 3H), 2.42 (br. s., 1H), 2.37-2.24 (m, 1H), 2.06-1.97 (m, 2H), 1.79-1.64 (m, 1H), 1.32 (s, 3H), 1.27-1.22 (m, 12H), 1.21-1.16 (m, 3H). LCMS (M+H)=711.6.

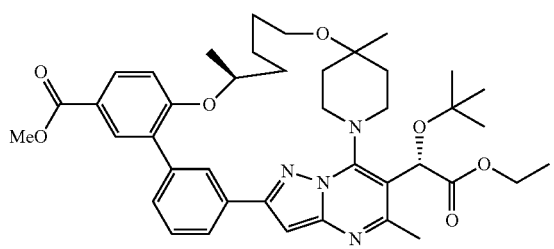 [SMILES: CCOC(=O)[C@@H](OC(C)(C)C)c1c(C)nc2cc3nn2c1N1CCC(C)(CC1)OCCCC[C@H](C)Oc1ccc(C(=O)OC)cc1-c1cccc-3c1]

Methyl (22S)-3-[(1S)-1-(tert-butoxy)-2-ethoxy-2-oxoethyl]-4, 22, 28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaene-17-carboxylate To a solution of (22S)-3-[(1S)-1-(tert-butoxy)-2-ethoxy-2-oxoethyl]-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaene-17-carboxylate (360 mg, 0.506 mmol) in Ethyl acetate (5 mL) was added 10% Pd/C (37.7 mg, 0.035 mmol) and the mixture was stirred under balloon hydrogen atmosphere for 3 h. At this point LCMS indicated completion of reaction. Mixture was then filtered through a pad of celite and the pad was washed with ethyl acetate. Filtrate was then concentrated to afford methyl (22S)-3-[(1S)-1-(tert-butoxy)-2-ethoxy-2-oxoethyl]-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaene-17-carboxylate (350 mg, 0.466 mmol, 92% yield) as off-white solid. $^1$H NMR (500 MHz, CDCl$_3$) δ 8.57 (s, 1H), 8.09-8.01 (m, 2H), 7.84 (d, J=7.9 Hz, 1H), 7.53 (t, J=7.6 Hz, 1H), 7.38 (d, J=7.6 Hz, 1H), 7.04 (d, J=8.5 Hz, 1H), 6.94 (br. s., 1H), 5.88 (br. s., 1H), 4.74-4.66 (m, 1H), 4.64-4.56 (m, 1H), 4.32-4.19 (m, 3H), 3.93 (s, 3H), 3.79 (t, J=12.0 Hz, 1H), 3.54-3.48 (m, 1H), 3.44-3.37 (m, 1H), 3.31 (d, J=12.6 Hz, 1H), 2.94 (d, J=9.8 Hz, 1H), 2.64 (s, 3H), 2.00 (d, J=12.0 Hz, 3H), 1.93-1.84 (m, 1H), 1.82-1.71 (m, 3H), 1.69-1.62 (m, 2H), 1.30-1.27 (m, 3H), 1.26-1.21 (m, 15H). LCMS (M+H)=713.6.

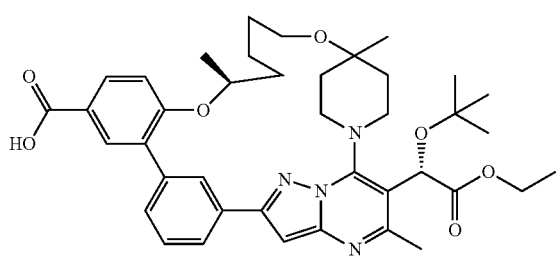 [SMILES: CCOC(=O)[C@@H](OC(C)(C)C)c1c(C)nc2cc3nn2c1N1CCC(C)(CC1)OCCCC[C@H](C)Oc1ccc(C(=O)O)cc1-c1cccc-3c1]

(22S)-3-[(S)-1-(tert-Butoxy)-2-ethoxy-2-oxoethyl]-4, 22, 28-trimethyl-21, 27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaene-17-carboxylic acid To a solution of methyl (22S)-3-[(1S)-1-(tert-butoxy)-2-ethoxy-2-oxoethyl]-4,22,28-trimethyl-21,27-dioxa-1,5,7,8-tetraazahexacyclo[26.2.2.21$^{6,9}$.1$^{10,14}$.0$^{2,7}$.0$^{15,20}$]tetratriaconta-2,4,6(34),8,10(33),11,13,15(20),16,18-decaene-17-carboxylate (340 mg, 0.477 mmol) in EtOH (4 mL) and THF (4 mL) was added 1N NaOH (0.525 mL, 0.525 mmol) and the resulting mixture was stirred at room temp for 16 h. Mixture was then concentrated and purified by prep HPLC to afford (22S)-3-[(1S)-1-(tert-butoxy)-2-ethoxy-2-oxoethyl]-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaene-17-carboxylic acid (35 mg, 0.048 mmol, 9.98% yield). $^1$H NMR (500 MHz, CDCl$_3$) δ 8.58 (s, 1H), 8.14-8.06 (m, 2H), 7.85 (d, J=7.9 Hz, 1H), 7.53 (t, J=7.7 Hz, 1H), 7.37 (d, J=7.7 Hz, 1H), 7.07 (d, J=9.6 Hz, 1H), 6.93 (s, 1H), 5.90 (br. s., 1H), 4.76-4.69 (m, 1H), 4.63 (t, J=12.0 Hz, 1H), 4.33-4.17 (m, 2H), 3.79 (t, J=11.7 Hz, 1H), 3.58-3.49 (m, 1H), 3.46-3.37 (m, 1H), 3.30 (d, J=11.8 Hz, 1H), 2.92 (d, J=11.0 Hz, 1H), 2.63 (s, 3H), 2.00 (d, J=13.2 Hz, 3H), 1.93-1.85 (m, 2H), 1.83-1.72 (m, 2H), 1.70-1.55 (m, 3H), 1.28 (d, J=4.6 Hz, 6H), 1.26-1.23 (m, 12H). LCMS (M+H)=699.5.

Example 25

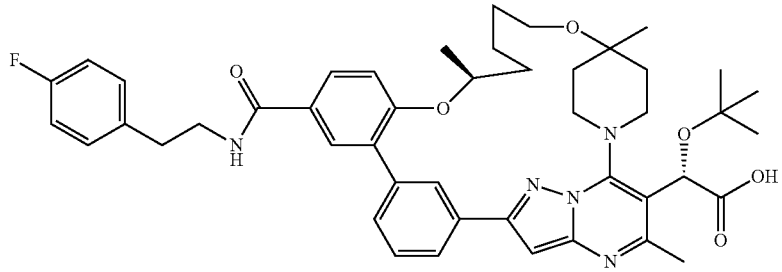 [SMILES: Cc1nc2cc3nn2c(c1[C@H](OC(C)(C)C)C(=O)O)N1CCC(C)(CC1)OCCCC[C@H](C)Oc1ccc(C(=O)NCCc2ccc(F)cc2)cc1-c1cccc-3c1]

(2S)-2-(tert-Butoxy)-2-[(22S)-17-{[2-(4-fluorophenyl)ethyl]carbamoyl}-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid To a solution of (22S)-3-[(1S)-1-(tert-butoxy)-2-ethoxy-2-oxoethyl]-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaene-17-carboxylic acid (12 mg, 0.017 mmol) and 2-(4-fluorophenyl)ethanamine (4.78 mg, 0.034 mmol) in DMF (0.5 mL) was added DIEA (0.015 mL, 0.086 mmol) followed by HATU (13.06 mg, 0.034 mmol) and DMAP (0.210 mg, 1.717 µmol) and the resulting mixture was stirred at room temp for 3 h. Water (2 mL) was then added and the mixture was extracted with ether (10 mL), washed with brine (2 mL), dried (Na$_2$SO$_4$), filtered and concentrated. The residue was then treated with 1N NaOH (0.086 mL, 0.086 mmol) in MeOH (0.5 mL) at 70° C. for 3 h. Mixture was then cooled and purified by prep HPLC to afford (2S)-2-(tert-butoxy)-2-[(22S)-17-{[2-(4- fluorophenyl)ethyl]carbamoyl}-4,22,28-trimethyl-21,27-dioxa-1,5,7,8-tetraazahexacyclo[26.2.2.1$^{6,9}$.1$^{10,14}$.0$^{2,7}$.0$^{15,20}$] tetratriaconta-2,4,6(34),8,10(33),11,13,15(20),16,18-decaen-3-yl]acetic acid (3.7 mg, 4.67 μmol, 27.2% yield). $^1$H NMR (500 MHz, DMSO-d$_6$) δ 8.52-8.45 (m, 2H), 7.96 (d, J=7.7 Hz, 1H), 7.85 (d, J=8.4 Hz, 1H), 7.81 (s, 1H), 7.57 (t, J=7.5 Hz, 1H), 7.39 (d, J=7.7 Hz, 1H), 7.30-7.22 (m, 3H), 7.15-7.07 (m, 3H), 5.59 (br. s., 1H), 4.81-4.68 (m, 1H), 4.53-4.41 (m, 1H), 3.61-3.53 (m, 3H), 3.51-3.39 (m, 5H), 2.88-2.78 (m, 3H), 2.00-1.88 (m, 3H), 1.74 (d, J=5.1 Hz, 2H), 1.68 (br. s., 2H), 1.60-1.51 (m, 1H), 1.49 (br. s., 2H), 1.18 (s, 3H), 1.16 (s, 9H), 1.12 (d, J=5.9 Hz, 3H). 4 missing piperidine hydrogens. LCMS (M+H)=792.6.

Example 26

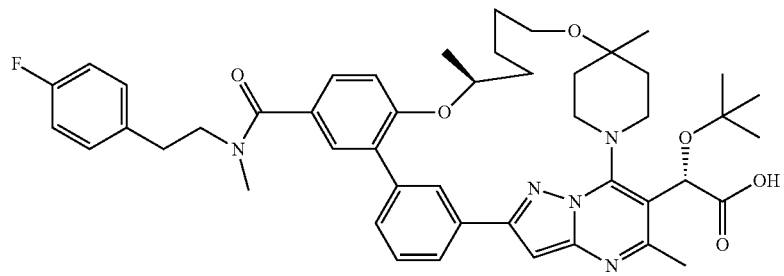

(2S)-2-(tert-Butoxy)-2-[(22S)-17-{[2-(4-fluorophenyl)ethyl](methyl)carbamoyl}-4, 22, 28-trimethyl-21, 27-dioxa-1, 5, 7, 8-tetraazahexacyclo[26.2.2.1$^{6,9}$.1$^{10,14}$.0$^{2,7}$.0$^{15,20}$]tetratriaconta-2,4,6(34),8,10 (33),11,13,15(20),16,18-decaen-3-yl]acetic acid To a solution of (22S)-3-[(1S)-1-(tert-butoxy)-2-ethoxy-2-oxoethyl]-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6 (34),8,10(33),11,13,15(20),16,18-decaene-17-carboxylic acid (12 mg, 0.017 mmol) and 2-(4-fluorophenyl)-N-methylethanamine (5.26 mg, 0.034 mmol) in DMF (0.5 mL) was added DIEA (0.015 mL, 0.086 mmol) followed by HATU (13.06 mg, 0.034 mmol) and DMAP (0.210 mg, 1.717 μmol) and the resulting mixture was stirred at room temp for 3 h. Water (2 mL) was then added and the mixture was extracted with ether (10 mL), washed with brine (2 mL), dried (Na$_2$SO$_4$), filtered and concentrated. The residue was then treated with 1N NaOH (0.086 mL, 0.086 mmol) in MeOH (0.5 mL) at 70° C. for 3 h. Mixture was then cooled and purified by prep HPLC to afford (2S)-2-(tert-butoxy)-2-[(22S)-17-{[2-(4-fluorophenyl)ethyl](methyl)carbamoyl}-4,22,28-trimethyl-21,27-dioxa-1,5,7,8-tetraazahexacyclo [26.2.2.1$^{6,9}$.1$^{10,14}$.0$^{2,7}$.0$^{15,20}$]tetratriaconta-2,4,6(34),8,10 (33),11,13,15(20),16,18-decaen-3-yl]acetic acid (5.4 mg, 6.70 μmol, 39.0% yield). $^1$H NMR (500 MHz, DMSO-d$_6$) δ 8.51 (br. s., 1H), 7.95 (d, J=7.7 Hz, 1H), 7.54 (br. s., 1H), 7.27 (br. s., 2H), 7.19 (br. s., 2H), 7.08 (br. s., 5H), 5.57 (br. s., 1H), 4.71 (br. s., 1H), 4.48 (br. s., 1H), 3.53-3.36 (m, 8H), 2.96 (br. s., 3H), 2.88 (d, J=11.7 Hz, 2H), 2.81 (br. s., 2H), 1.92 (d, J=11.4 Hz, 3H), 1.73 (br. s., 2H), 1.67 (br. s., 2H), 1.54 (br. s., 1H), 1.48 (br. s., 2H), 1.24-1.00 (m, 15H). LCMS (M+H)=806.6.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound selected from the group consisting of (2S)-2-(tert-Butoxy)-2-{18-fluoro-4-methyl-21,28-dioxa-5,7,8-triazahexacyclo[27.2.2.1$^{6,9}$.1$^{10,14}$.0$^{2,7}$.0$^{15,20}$]pentatriaconta-1(31),2,4,6(35),8,10(34),11,13,15(20),16,18,29,32-tridecaen-3-yl}acetic acid;

(2S)-2-(tert-Butoxy)-2-[(23E)-18-fluoro-4-methyl-21,26-dioxa-5,7,8-triazahexacyclo[25.2.2.1$^{6,9}$.1$^{10,14}$.0$^{2,7}$.0$^{15,20}$]tritriaconta-1(29),2,4,6(33),8,10(32),11,13,15(20),16,18,23,27,30-tetradecaen-3-yl]acetic acid;

(2S)-2-(tert-Butoxy)-2-{18-fluoro-4-methyl-21,29-dioxa-5,7,8-triazaheptacyclo[28.2.2.1$^{6,9}$.1$^{10,14}$.1$^{23,27}$.0$^{2,7}$.0$^{15,20}$]heptatriaconta-1(32),2,4,6(37),8,10(36),11,13,15(20),16,18,23(35),24,26,30,33-hexadecaen-3-yl}acetic acid;

(2S)-2-(tert-Butoxy)-2-{18-fluoro-4-methyl-21,26-dioxa-5,7,8-triazahexacyclo[25.2.2.1$^{6,9}$.1$^{10,14}$.0$^{2,7}$.0$^{15,20}$]tritriaconta-1(29),2,4,6(33),8,10(32),11,13,15(20),16,18,27,30-tridecaen-23-yn-3-yl}acetic acid;

(2S)-2-(tert-Butoxy)-2-{18-fluoro-4-methyl-21,24,27-trioxa-5,7,8-triazahexacyclo[26.2.2.1$^{6,9}$.1$^{10,14}$.0$^{2,7}$.0$^{15,20}$] tetratriaconta-1(30),2,4,6(34),8,10(33),11,13,15(20),16,18,28,31-tridecaen-3-yl}acetic acid;

(2S)-2-(tert-Butoxy)-2-{22-fluoro-7,13-dimethyl-17-methylidene-15,19-dioxa-3,4,6-triazahexacyclo [24.3.1.1$^{2,5}$.1$^{10,14}$.0$^{4,9}$.0$^{20,25}$]dotriaconta-1(30),2,5 (32),6,8,10,12,14(31),20(25),21,23,26,28-tridecaen-8-yl}acetic acid;

(2S)-2-(tert-Butoxy)-2-[(17E)-23-fluoro-7,13-dimethyl-15,20-dioxa-3,4,6-triazahexacyclo[25.3.1.1$^{2,5}$.1$^{10,14}$.0$^{4,9}$.0$^{21,26}$]tritriaconta-1(31),2,5(33),6,8,10,12,14(32),17,21(26),22,24,27,29-tetradecaen-8-yl]acetic acid;

(2S)-2-(tert-Butoxy)-2-{26-fluoro-7,13-dimethyl-15,23-dioxa-3,4,6,35-tetraazaheptacyclo[28.3.1.1$^{2,5}$.1$^{10,14}$.1$^{17,21}$.0$^{4,9}$.0$^{24,29}$]heptatriaconta-1(34),2,5(37),6,8,10,12,14(36),17(35),18,20,24(29),25,27,30,32-hexadecaen-8-yl}acetic acid;

(2S)-2-(tert-Butoxy)-2-[(17Z)-23-fluoro-7,13-dimethyl-15,20-dioxa-3,4,6-triazahexacyclo[25.3.1.1$^{2,5}$.1$^{10,14}$.0$^{4,9}$.0$^{21,26}$]tritriaconta-1(31),2,5(33),6,8,10,12,14(32),17,21(26),22,24,27,29-tetradecaen-8-yl]acetic acid;

(2S)-2-(tert-Butoxy)-2-{18,18,19,19,25-pentafluoro-7,13-dimethyl-15,22-dioxa-3,4,6-triazahexacyclo [27.3.1.1$^{2,5}$.1$^{10,14}$.0$^{4,9}$.0$^{23,28}$]pentatriaconta-1(33),2,5(35),6,8,10,12,14(34),23(28),24,26,29,31-tridecaen-8-yl}acetic acid;

(2S)-2-(tert-Butoxy)-2-{23-fluoro-7,13-dimethyl-15,20-dioxa-3,4,6-triazahexacyclo[25.3.1.1$^{2,5}$.1$^{10,14}$.0$^{4,9}$.0$^{21,26}$]tritriaconta-1(31),2,5(33),6,8,10,12,14(32),21(26),22,24,27,29-tridecaen-17-yn-8-yl)}acetic acid;

(2S)-2-(tert-Butoxy)-2-{18-tert-butyl-24-fluoro-7,13-dimethyl-15,21-dioxa-3,4,6,18-tetraazahexacyclo[26.3.1.1$^{2,5}$.1$^{10,14}$.0$^{4,9}$.0$^{22,27}$]tetratriaconta-1(32),2,5(34),6,8,10,12,14(33),22(27),23,25,28,30-tridecaen-8-yl}acetic acid;

(2S)-2-(tert-Butoxy)-2-{26-fluoro-7,13-dimethyl-15,23-dioxa-3,4,6-triazaheptacyclo[28.3.1.1$^{2,5}$.1$^{10,14}$.1$^{17,21}$.0$^{4,9}$.0$^{24,29}$]heptatriaconta-1(34),2,5(37),6,8,10,12,14(36),17(35),18,20,24(29),25,27,30,32-hexadecaen-8-yl}acetic acid;

(2S)-2-(tert-Butoxy)-2-{13,23-difluoro-7-methyl-18-methylidene-16,20-dioxa-3,4,6-triazahexacyclo[25.3.1.1$^{2,5}$.0$^{4,9}$.0$^{10,15}$.0$^{21,26}$]dotriaconta-1(31),2,5(32),6,8,10,12,14,21(26),22,24,27,29-tridecaen-8-yl}acetic acid;

(2S)-2-(tert-Butoxy)-2-{18-fluoro-4-methyl-21,27,31-trioxa-5,7,8-triazaheptacyclo[26.6.2.1$^{6,9}$.1$^{10,14}$.0$^{2,7}$.0$^{15,20}$.0$^{32,36}$]octatriaconta-1(34),2,4,6(38),8,10(37),11,13,15(20),16,18,32,35-tridecaen-3-yl}acetic acid (2S)-2-(tert-Butoxy)-2-{18-fluoro-4-methyl-21,28,32-trioxa-5,7,8-triazaheptacyclo[27.6.2.1$^{6,9}$.1$^{10,14}$.0$^{2,7}$.0$^{15,20}$.0$^{33,37}$]nonatriaconta-1(35),2,4,6(39),8,10(38),11,13,15(20),16,18,33,36-tridecaen-3-yl}acetic acid;

(2S)-2-(tert-Butoxy)-2-{18-fluoro-4,28-dimethyl-21,24,27-trioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl}acetic acid;

(2S)-2-(tert-butoxy)-2-{18-fluoro-4-methyl-21,29-dioxa-5,7,8-triazaoctacyclo[28.6.2.1$^{6,9}$.1$^{10,14}$.1$^{23,27}$.0$^{2,7}$.0$^{15,20}$.0$^{31,36}$]hentetraconta-1(37),2,4,6(41),8,10(40),11,13,15(20),16,18,23(39),24,26,30(38),31 (36),32,34-octadecaen-3-yl}acetic acid;

(2S)-2-(tert-butoxy)-2-{18-fluoro-4-methyl-21,26-dioxa-5,7,8-triazaheptacyclo[25.6.2.1$^{6,9}$.1$^{10,14}$.0$^{2,7}$.0$^{15,20}$.0$^{28,33}$]heptatriaconta-1(34),2,4,6(37),8,10(36),11,13,15(20),16,18,27(35),28(33),29,31-pentadecaen-23-yn-3-yl}acetic acid;

(2S)-2-(tert-butoxy)-2-{25-fluoro-7,13-dimethyl-15,22-dioxa-3,4,6-triazahexacyclo[27.3.1.1$^{2,5}$.1$^{10,14}$.0$^{4,9}$.0$^{23,28}$]pentatriaconta-1(33),2,5(35),6,8,10,12,14(34),23(28),24,26,29,31-tridecaen-8-yl}acetic acid;

(2S)-2-(tert-butoxy)-2-{24-fluoro-7,13-dimethyl-15,18,21-trioxa-3,4,6-triazahexacyclo[26.3.1.1$^{2,5}$.1$^{10,14}$.0$^{4,9}$.0$^{22,27}$]tetratriaconta-1(32),2,5(34),6,8,10,12,14(33),22(27),23,25,28,30-tridecaen-8-yl}acetic acid;

(2S)-2-(tert-butoxy)-2-{18-fluoro-4-methyl-21,29,33-trioxa-5,7,8-triazaoctacyclo[28.6.2.1$^{6,9}$.1$^{10,14}$.1$^{23,27}$.0$^{2,7}$.0$^{15,20}$.0$^{34,38}$]hentetraconta-1(36),2,4,6(41),8,10(40),11,13,15(20),16,18,23,25,27(39),34,37-hexadecaen-3-yl}acetic acid;

(2S)-2-(tert-butoxy)-2-{25-fluoro-7,13-dimethyl-16,22-dioxa-3,4,6-triazahexacyclo[27.3.1.1$^{2,5}$.0$^{4,9}$.0$^{10,15}$.0$^{34,38}$]tetratriaconta-1(33),2,5(34),6,8, 10,12,14,23(28),24,26,29,31-tridecaen-8-yl}acetic acid;

(2S)-2-(tert-butoxy)-2-{18-fluoro-4-methyl-21,29,33-trioxa-5,7,8-triazaoctacyclo[28.6.2.1$^{6,9}$.1$^{10,14}$.1$^{23,27}$.0$^{2,7}$.0$^{15,20}$.0$^{34,38}$]hentetraconta-1(36),2,4,6(41),8,10(40),11,13,15(20),16,18,23,25,27(39),34,37-hexadecaen-3-yl}acetic acid;

(2S)-2-(tert-Butoxy)-2-[(22S)-17-{[2-(4-fluorophenyl)ethyl]carbamoyl}-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid; and (2S)-2-(tert-Butoxy)-2-[(22S)-17-{[2-(4-fluorophenyl)ethyl](methyl)carbamoyl}-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

and pharmaceutically acceptable salts at thereof.

2. A pharmaceutical composition comprising a compound or salt of claim 1 and a pharmaceutically acceptable carrier.

3. A method for treating HIV infection comprising administering a compound or salt of claim 1 to a patient in need thereof.

4. The method of claim 3 further comprising administering a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

* * * * *